US010280465B2

(12) United States Patent
Rus et al.

(10) Patent No.: US 10,280,465 B2
(45) Date of Patent: May 7, 2019

(54) BIOMARKERS FOR PREDICTING RELAPSE IN MULTIPLE SCLEROSIS

(71) Applicants: The United States of America as represented by the Department of Veteran Affairs, Department of Veterans Affairs, Washington, DC (US); University of Maryland, Baltimore, Baltimore, MD (US)

(72) Inventors: Horea G. Rus, Catonsville, MD (US); Cosmin A. Tegla, Bronx, NY (US)

(73) Assignees: UNIVERSITY OF MARYLAND, BALTIMORE, Baltimore, MD (US); THE UNITED STATES OF AMERICA AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 356 days.

(21) Appl. No.: 14/978,772

(22) Filed: Dec. 22, 2015

(65) Prior Publication Data

US 2016/0194714 A1    Jul. 7, 2016

Related U.S. Application Data

(60) Provisional application No. 62/096,005, filed on Dec. 23, 2014.

(51) Int. Cl.
*C12Q 1/68* (2018.01)
*C12Q 1/6883* (2018.01)
*G01N 33/68* (2006.01)

(52) U.S. Cl.
CPC ....... *C12Q 1/6883* (2013.01); *G01N 33/6896* (2013.01); *C12Q 2600/106* (2013.01); *C12Q 2600/112* (2013.01); *C12Q 2600/158* (2013.01); *G01N 2333/525* (2013.01); *G01N 2333/54* (2013.01); *G01N 2333/978* (2013.01); *G01N 2800/285* (2013.01); *G01N 2800/54* (2013.01)

(58) Field of Classification Search
None
See application file for complete search history.

(56) References Cited

PUBLICATIONS

Tegla et al; Experimental and Molecular Pathology, vol. 96, pp. 139-148; Jan. 5, 2014.*
Kruszewski, Adam M. et al., "RGC-32 as a potential biomarker of relapse and response to treatment with glatiramer acetate in multiple sclerosis", *Experimental and Molecular Pathology*, 2015, vol. 99, pp. 498-505.
Tegla, Cosmin A. et al., "SIRT1 is decreased during relapses in patients with multiple sclerosis", *Experimental and Molecular Pathology*, 2014, vol. 96, No. 2, pp. 139-148.

* cited by examiner

*Primary Examiner* — Jehanne S Sitton
(74) *Attorney, Agent, or Firm* — Wenderoth, Lind & Ponack, L.L.P.

(57) ABSTRACT

Methods of determining relapse in subjects having relapsing-remitting multiple sclerosis (RRMS) and predicting their response to glatiramer acetate (GA) using the biomarkers SIRT1, RGC-32, FasL and IL-21 are presented.

8 Claims, 17 Drawing Sheets
Specification includes a Sequence Listing.

AUC = 88.00% (p=0.047)
Cut-Off < 0.645
    Sensitivity = 80% (95% CI 28-99)
    Specificity = 80% (95% CI 28-99)

SEQUENCE LISTING

```
<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: PCR primer

<400> SEQUENCE: 1
tggcaaagga gcagattagt ag                                              22

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2
ggcatgtccc actatcactg t                                               21

<210> SEQ ID NO 3
<211> LENGTH: 22
<212> TYPE: DNA
<213> ORGANISM: Artificial Sequence
<220> FEATURE:
<223> OTHER INFORMATION: PCR primer

<400> SEQUENCE: 3
catgcaccta gtgtccagat tc                                              22

<210> SEQ ID NO 4
<211> LENGTH: 22
<212> TYPE: DNA
<213> ORGANISM: Artificial Sequence
<220> FEATURE:
<223> OTHER INFORMATION: PCRF primer

<400> SEQUENCE: 4
cactcttaaa tctccacatc gc                                              22

<210> SEQ ID NO 5
<211> LENGTH: 20
<212> TYPE: DNA
<213> ORGANISM: Artificial Sequence
<220> FEATURE:
<223> OTHER INFORMATION: PCR primer
```

<400> SEQUENCE: 5
aggaacagct tcagcttcag                                              20

<210> SEQ ID NO 6
<211> LENGTH: 24
<212> TYPE: DNA
<213> ORGANISM: Artificial Sequence
<220> FEATURE:
<223> OTHER INFORMATION: PCR primer

<400> SEQUENCE: 6
gctaaagttt tgtcaagatc agca                                         24

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
gcccatttaa caggcaagtc                                              20

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
atcacaaggc caccttctt                                               20

<210> SEQ ID NO 9
<211> LENGTH: 19
<212> TYPE: DNA
<213> ORGANISM: Artificial Sequence
<220> FEATURE:
<223> OTHER INFORMATION: PCR primer

<400> SEQUENCE: 9
cgtgcgtctg aagcctaca                                               19

<210> SEQ ID NO 10
<211> LENGTH: 19
<212> TYPE: DNA
<213> ORGANISM: Artificial Sequence
<220> FEATURE:
<223> OTHER INFORMATION: PCR primer

<400> SEQUENCE: 10
ggagtccgtg ggtcttgag                                               19

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
ttttcagagc tttgggcact                                              20

<210> SEQ ID NO 12
<211> LENGTH: 20

```
<212> TYPE: DNA
<213> ORGANISM: Artificial Sequence
<220> FEATURE:
<223> OTHER INFORMATION: PCR primer

<400> SEQUENCE: 12
aggcttcctg gtttccattt                                               20

<210> SEQ ID NO 13
<211> LENGTH: 18
<212> TYPE: DNA
<213> ORGANISM: Artificial Sequence
<220> FEATURE:
<223> OTHER INFORMATION: PCR primer

<400> SEQUENCE: 13
acgccaagga gatcatgc                                                 18

<210> SEQ ID NO 14
<211> LENGTH: 21
<212> TYPE: DNA
<213> ORGANISM: Artificial Sequence
<220> FEATURE:
<223> OTHER INFORMATION: PCR primer

<400> SEQUENCE: 14
ctccatgctg tcatcttggt c                                             21
```

BIOMARKERS FOR PREDICTING RELAPSE IN MULTIPLE SCLEROSIS

BACKGROUND OF INVENTION

Multiple sclerosis (MS) is a demyelinating disease characterized by chronic inflammation of the central nervous system in which many factors (genetic and environmental) may act together to influence disease susceptibility and progression (Frohman et al., 2006; Keegan and Noseworthy, 2002). While a large body of work has enhanced an understanding of the fundamental nature of MS, basic research into its etiology, pathophysiology, and treatment faces enormous challenges, and this may in part be due to the great variability in the clinical presentation and course of MS (Compston and Coles, 2008; Frohman et al., 2006; Keegan and Noseworthy, 2002).

Relapsing-remitting multiple sclerosis (RRMS) is one of the two main forms of the disease, the other being primary-progressive multiple sclerosis (PPMS). RRMS is characterized by periods of worsening neurologic function (Lublin et al., 2014; Polman et al., 2011). These periods, termed relapses or flare-ups, are followed by partial or complete recovery periods (remissions), during which symptoms improve partially or completely, and there is no apparent disease progression. RRMS is the most common disease course at the time of diagnosis (Lublin et al., 2014; Polman et al., 2011). Approximately 85 percent of people are initially diagnosed with RRMS, compared to 10-15 percent with progressive forms of the disease (Lublin et al., 2014; Polman et al., 2011). RRMS is defined by inflammatory attacks on myelin, as well as the nerve fibers themselves (Lublin et al., 2014; Polman et al., 2011). During these inflammatory attacks, activated immune cells cause small, localized areas of damage which produce the symptoms of MS (Lublin et al., 2014; Polman et al., 2011). Because the location of the damage is so variable, no two people have exactly the same symptoms.

While RRMS is defined by attacks of inflammation (relapses) in the central nervous system (CNS), the progressive form of MS involves much less of this type of inflammation. Subjects with RRMS tend to have more brain lesions, also called plaques or scars, detectable via magnetic resonance imaging (MRI) scans, and these lesions contain more inflammatory cells. Subjects with PPMS tend to have more spinal cord lesions, which contain fewer inflammatory cells.

A subject is diagnosed as having RRMS when test results provide evidence of at least two separate areas of damage to the myelin in the CNS that have occurred at different points in time (nationalmssociety.org). Tests that may be used to determine whether there is relevant damage to myelin in a subject include magnetic resonance imaging (MRI), visual evoked potential (VEP) testing, and analysis of the cerebrospinal fluid (nationalmssociety.org).

These tests have drawbacks, including pain, risks and costs. For example, a brain MRI is an expensive test that is hard to tolerate by claustrophobic patients. In addition, identification of active lesions on a brain Mill requires the administration of the gadolinium to a subject, which poses significant risks of allergic reactions and gadolinium-associated nephrogenic systemic fibrosis (Grobner T., 2006; Hellman, R., 2011). Indeed, gadolinium associated nephrogenic systemic fibrosis is a systemic, sometimes fatal (mortality rate up to 30%), disabling disease, mimicking scleroderma (Grobner T., 2006; Hellman, R., 2011).

The development of additional means for diagnosing a subject as having RRMS or determining whether a subject already diagnosed with MS is experiencing a relapse will greatly aid clinicians in quickly and accurately prescribing appropriate treatment. The present invention is directed to these and other important goals.

BRIEF SUMMARY OF INVENTION

The present invention is generally directed to the use of sirtuin 1 (SIRT1), RGC-32, FasL and IL-21 as biomarkers in determining whether a subject previously diagnosed as having relapsing-remitting multiple sclerosis (RRMS) is undergoing a relapse of the disease and to predicting whether a subject having RRMA will respond to treatment with glatiramer acetate (GA).

The invention is derived from the investigations conducted by the inventors and presented herein. As discussed in detail below, the inventors studied the expression of several biomarkers, including SIRT1, RGC-32, FasL and IL-21, in RRMS patients undergoing relapse (relapse RRMS) and compared expression levels to those of healthy controls and RRMS patients not experiencing relapse (stable RRMS). Levels of SIRT1, RGC-32 and FasL mRNA and protein were found to be significantly reduced in RRMS patients with relapse as compared to control patients, while levels of IL-21 mRNA and protein were found to be increased. Thus, it was found that changes in the expression levels of these four molecules could be used as markers of disease activity in patients with RRMS.

In a first embodiment, the invention is generally drawn to methods for determining whether a subject having relapsing-remitting multiple sclerosis (RRMS) is undergoing relapse of the disease by monitoring levels of mRNA expression of certain biomarkers. In particular, the invention is drawn to methods for determining whether a subject having relapsing-remitting multiple sclerosis (RRMS) is undergoing relapse of the disease, comprising (i) determining mRNA expression levels for one or more biomarkers selected from the group consisting of SIRT1, RGC-32, FasL and IL-21 in a population of cells, (ii) determining mRNA expression levels for L13 in the same population of cells, and (iii) calculating a ratio of biomarker mRNA expression to L13 mRNA expression, wherein when the biomarker is SIRT1 and the SIRT1/L13 ratio is <3.06±10%, the subject is determined to be undergoing relapse, wherein when the biomarker is RGC-32 and the RGC-32/L13 ratio is <1.27±10%, the subject is determined to be undergoing relapse, wherein when the biomarker is FasL and the FasL/L13 ratio is <52.6±10%, the subject is determined to be undergoing relapse, and wherein when the biomarker is IL-21 and the IL-21/L13 ratio is >16.9±10%, the subject is determined to be undergoing relapse.

In certain aspects of this embodiment, when the biomarker is SIRT1, the SIRT1/L13 ratio is about <3.06. In certain aspects of this embodiment, when biomarker is RGC-32, the RGC-32/L13 ratio is about <1.27. In certain aspects of this embodiment, when the biomarker is FasL, the FasL/L13 ratio is about <52.6. In certain aspects of this embodiment, when the biomarker is IL-21, the IL-21/L13 ratio is about >16.9.

In certain aspects of this embodiment, mRNA expression levels for one, two, three or all of the four biomarkers is determined.

In certain aspects of this embodiment, when the subject is determined to be undergoing relapse, the method further comprises administering a therapeutically effective amount of a treatment for RRMS to the subject. The treatment may be, for example, glatiramer acetate (GA), beta-interferons, teriflunomide, fingolimod, dimethyl fumarate, and natalizumab.

In a second embodiment, the invention is generally drawn to methods for determining whether a subject having relapsing-remitting multiple sclerosis (RRMS) is undergoing relapse of the disease by monitoring levels of protein expression of certain biomarkers. In particular, the invention is drawn to methods for determining whether a subject having relapsing-remitting multiple sclerosis (RRMS) is undergoing relapse of the disease, comprising (i) determining protein expression levels for SIRT1 in a population of cells, (ii) determining protein expression levels for L13 in the same population of cells, and (iii) calculating a ratio of SIRT1 protein expression to L13 protein expression, wherein when the SIRT1/L13 ratio is <0.645±10%, the subject is determined to be undergoing relapse.

In certain aspects of this embodiment, the SIRT1/L13 ratio is about <0.645.

In certain aspects of this embodiment, when the subject is determined to be undergoing relapse, the method further comprises administering a therapeutically effective amount of a treatment for RRMS to the subject. The treatment may be, for example, glatiramer acetate (GA), beta-interferons, teriflunomide, fingolimod, dimethyl fumarate, and natalizumab.

In a third embodiment, the invention is generally drawn to methods for determining whether a subject having relapsing-remitting multiple sclerosis (RRMS) will respond to treatment with glatiramer acetate (GA). In particular, the invention is drawn to methods for determining whether a subject having relapsing-remitting multiple sclerosis (RRMS) will respond to treatment with GA, comprising (i) determining mRNA expression levels for one or more biomarkers selected from the group consisting of SIRT1, RGC-32, FasL and IL-21 in a population of cells, (ii) determining mRNA expression levels for L13 in the same population of cells, and (iii) calculating a ratio of biomarker mRNA expression to L13 mRNA expression, wherein when the biomarker is SIRT1 and the SIRT1/L13 ratio is >4.33±10%, it is determined that the subject will respond to treatment with GA, wherein when the biomarker is RGC-32 and the RGC-32/L13 ratio is >2.52±10%, it is determined that the subject will respond to treatment with GA, wherein when the biomarker is FasL and the FasL/L13 ratio is >85.4±10%, it is determined that the subject will respond to treatment with GA, and wherein when the biomarker is IL-21 and the IL-21/L13 ratio is <11.9±10%, it is determined that the subject will respond to treatment with GA.

In certain aspects of this embodiment, when the biomarker is SIRT1, the SIRT1/L13 ratio is about >4.33. In certain aspects of this embodiment, when biomarker is RGC-32, the RGC-32/L13 ratio is about >2.52. In certain aspects of this embodiment, when the biomarker is FasL, the FasL/L13 ratio is about >85.4. In certain aspects of this embodiment, when the biomarker is IL-21, the IL-21/L13 ratio is about <11.9.

In certain aspects of this embodiment, mRNA expression levels for one, two, three or all of the four biomarkers is determined.

In certain aspects of this embodiment, when it is determined that the subject will respond to treatment with GA, the method further comprises administering a therapeutically effective amount of GA to the subject. When it is determined that the subject will not respond to treatment with GA, the method further comprises administering a therapeutically effective amount of another, non-GA treatment suitable for RRMS including, but not limited to, beta-interferons, teriflunomide, fingolimod, dimethyl fumarate, and natalizumab.

In each of the embodiments and aspects of the invention, the population of cells may be, but is not limited to, peripheral blood mononuclear cells (PBMCs), CD4+ T cells, CD8+ T cells, MAB328+ cells, GFAP+ cells, leukocytes, monocytes, glial cells, dendritic cells, and neurons.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

(FIG. 1A) Perivascular deposits of SIRT1 on inflammatory cells in MS plaque (arrows). (FIG. 1B) Parenchymal deposits of SIRT1 in normal adjacent gray matter; some positive cells have morphology suggestive of glial cells (arrows). (FIG. 1C) Perivascular deposits of p-SIRT1 on perivascular cells in an MS plaque. P-SIRT1 deposits are localized to the nucleus (arrows). Hematoxylin was not used for counterstaining in this experiment. (FIG. 1D) Control for the immunoperoxidase reaction. FIGS. 1A-1D: original magnification, ×400.

(FIG. 2A) Perivascular deposits of HDAC3 on inflammatory cells in an MS plaque (arrows). (FIG. 2B) Parenchymal deposits of HDAC3, which are localized to the nucleus (arrows). Hematoxylin was not used for counterstaining in this experiment. (FIG. 2C) Perivascular deposits of p-HDAC3 on inflammatory cells in normal adjacent white matter. Some positive cells have morphology suggestive of glial cells (arrows).

pHDAC3 was localized both in the cytoplasm and in the nucleus. (FIG. 2D) Control for the immunoperoxidase reaction. FIGS. 2A-2D: original magnification, ×400.

FIG. 3A, FIG. 3B. SIRT1-expressing cells were co-localized by double staining. (FIG. 3A) By double-staining, some of the SIRT1-positive cells are seen to be co-localized with CD4 T cells in an MS plaque (arrows and insert). Not all the SIRT1-positive cells in parenchymal areas express CD4. (FIG. 3B) SIRT1-positive cells are seen to be co-localized with CD68 in an MS plaque (arrows). (FIG. 3C) SIRT1-positive cells are also co-localized with OLG in an MS plaque (arrows). Almost all OLG have nuclear deposits of SIRT1. (FIG. 3D) SIRT1-positive cells are co-localized with GFAP in an MS plaque (arrows). (FIG. 3E) Staining of the same area as in FIGS. 3A-3D for myelin/OLG using MAB328 shows significant demyelination in an MS plaque. (FIG. 3F) Control for the immunoperoxidase reaction. Original magnification: FIGS. 3A-3D (×400); FIG. 3E (×100); FIG. 3F (×400); Inserts, (×1000).

(FIG. 4A) A statistically significant decrease in SIRT1 was found in patients with relapse when compared to controls ($p<0.04$). (FIG. 4B) Levels of HDAC3 mRNA in MS patients were similar to those in controls. (FIG. 4C) SIRT1 protein expression was significantly decreased in the MS patients with relapses when compared to both stable MS patients and controls.

(FIG. 5A) An example of a western blot relevant to the expression of histone H3K9ac (upper panel). Higher levels of H3K9ac were found during relapses ($p<0.05$). Results are expressed as ratios to beta-actin (lower panel). (FIG. 5B) An example of a western blot relevant to the expression of histone H3K9me2 (upper panel). Levels of H3K9me2 in MS patients did not differ significantly from those in controls. Results are expressed as ratios to beta-actin (lower panel). (FIG. 5C, FIG. 5D) Correlation of SIRT1 with histone H3K9ac and H3K9me2 expression by Spearman's correlation coefficient. SIRT1 protein levels were positively correlated with levels of H3K9ac ($R=0.544$, $p=0.0196$) (FIG. 5C) and H3K9me2 ($R=0.716$, $p=0.0008$) (FIG. 5D).

(FIG. 6A) RGC-32 shRNA treatment effectively decreased mRNA RGC-32 expression by 78% when compared to shRNA control (shCTR)-transfected cells. (FIG. 6B) SIRT1 mRNA expression was reduced by 50% ($p=0.01$), indicating an important role for RGC-32 in mediating SIRT1 mRNA expression.

(FIG. 11A) In the present cohort, a SIRT1/L13 ratio<3.06 detected patient relapse with specificity of 81%. (FIG. 11B) A SIRT1/L13 ratio>4.33 detected patient response to GA therapy with a specificity of 73%. AUC, represented as a percentage, with a perfect score being 100% predictability.

(FIG. 13A) Significantly lower levels of RGC-32 mRNA were found in patients with relapses compared to clinically stable patients ($p<0.0001$). (FIG. 13B) Significantly lower levels of FasL mRNA were found in patients with relapses compared to clinically stable patients ($p<0.0001$). (FIG. 13C; FIG. 13D) No statistically significant changes were observed in CDC2 or AKT mRNA. (FIG. 13E) Significantly higher levels of IL-21 mRNA were found in patients with relapses compared to clinically stable patients ($p=0.04$). (FIG. 13) RGC-32 mRNA expression levels were correlated with those of FasL in patients during relapses ($r=0.90$, p b 0.0001).

(FIG. 14A) Significantly higher levels of RGC-32 mRNA were found in responders to GA compared to non-responders (p<0.0001). (FIG. 14B) Significantly higher levels of FasL mRNA were found in responders to GA compared to non-responders (p<0.0001). (FIG. 14C; FIG. 14D) Levels of CDC2 and AKT mRNA were not significantly different between responders to GA and non-responders. (FIG. 14E) Significantly decreased levels of IL-21 mRNA were found in responders to GA compared to non-responders (p=0.02).

(FIG. 15A) Responders to GA showed persistently higher levels of RGC-32 compared to non-responders over time. (FIG. 15B) A similar pattern was observed for FasL mRNA expression, with higher levels of mRNA expression seen in responders and lower levels in non-responders over time. (FIG. 15C) Responders to GA showed persistently lower levels of IL-21 compared to non-responders over time.

(FIG. 17A) In the present cohort, a RGC-32/L13 ratio<1.27 detected patient relapse with a sensitivity of 71% and a specificity of 95%. (FIG. 17B) A FasL/L13 ratio<52.6 detected patient relapse with a sensitivity of 81% and a specificity of 95%. (FIG. 17C) An IL-21/L13 ratio>16.9 detected patient relapse with a sensitivity of 54% and a specificity of 88%.

(FIG. 18A) In the present cohort, a RGC-32/L13 ratio>2.52 detected RRMS patient response to GA with a sensitivity of 71% and a specificity of 92%. (FIG. 18B) A FasL/L13 ratio>85.4 detected RRMS patient response to GA with a sensitivity of 85% and a specificity of 92%. (FIG. 18C) An IL-21/L13 ratio<11.9 detected RRMS patient response to GA with a sensitivity of 81% and a specificity of 89%.

DETAILED DESCRIPTION OF THE INVENTION

I. Definitions

Figures 1A, 1B, 1C, 1D:
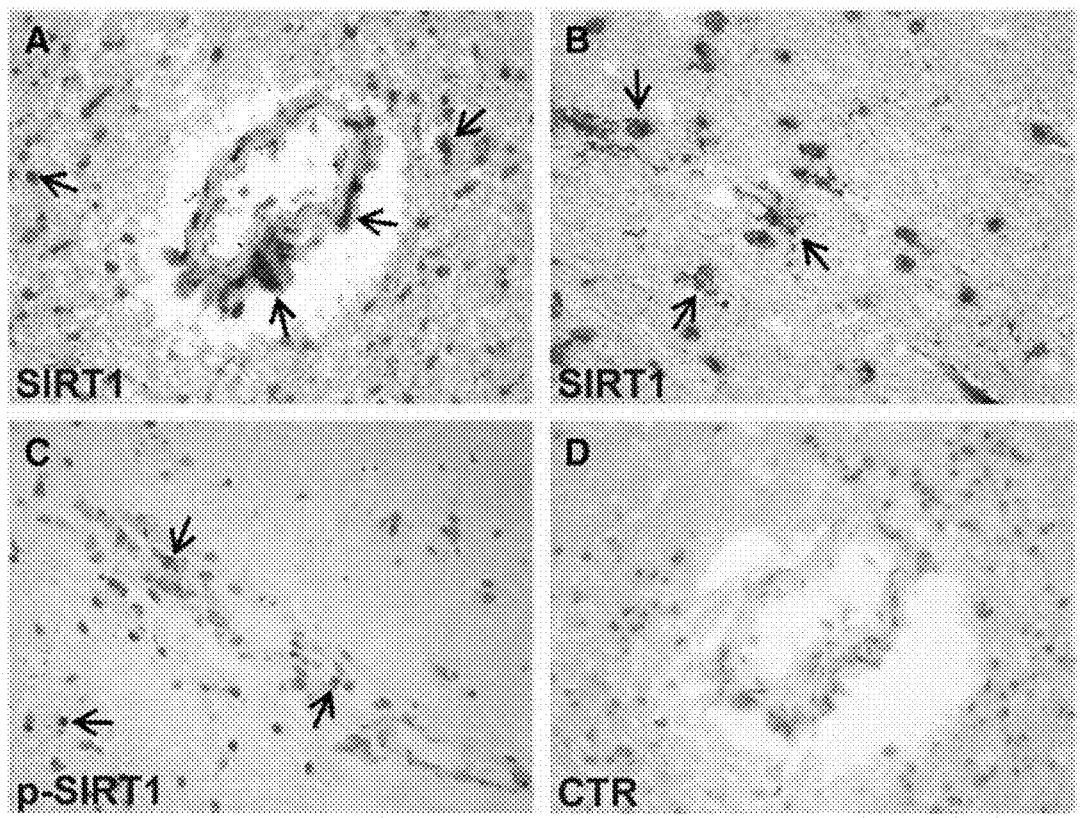
FIGS. 1A-1D. Immunohistochemical staining for SIRT1 and phosphorylated SIRT1 (p-SIRT1) in MS brains. SIRT1 and phosphorylated SIRT1 ("p-SIRT1") were localized in MS brain by immunostaining.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

As briefly summarized above, the present inventors have found that the levels of the biomarkers SIRT1, RGC-32, FasL and IL-21 vary in a subject having RRMS based on the whether the subject is experiencing a relapse. Among other observations, the inventors found SIRT1 levels were significantly reduced in MS patients with relapses as compared to control patients. In particular, decreased expression of SIRT1 was found in PBMCs during relapse, thus demonstrating the protein may be used as a marker of disease activity. These observations form the basis of the present invention which is generally directed to methods for determining whether a subject previously diagnosed as having MS is undergoing a relapse of the disease and to predicting whether a subject having RRMS will respond to treatment with glatiramer acetate (GA) based on expression levels of the biomarkers SIRT1, RGC-32, FasL and IL-21.

Sirtuin 1 (SIRT1) is a member of the HDAC (histone deacetylase) class III family of proteins (Smith et al., 2000). It is an NADtdependent histone and protein deacetylase (Penberthy and Tsunoda, 2009; Smith et al., 2000) that catalyzes the removal of acetyl groups from a variety of protein substrates (Turner, 1998), including histones H1, H3, and H4 (Turner, 1998; Wang et al., 2011; Zhang and Kraus, 2010). In addition, SIRT1 has been found to promote histone H3K9 methylation, resulting in epigenetic gene silencing (Imai et al., 2000; Vaquero et al., 2007; Vaquero et al., 2004). SIRT1 is involved in the regulation of a number of cellular processes, including transcription, metabolism (Chen et al., 2008; He et al., 2012), DNA repair, and aging (Guarente, 2011). SIRT1 can induce chromatin silencing through the deacetylation of histones (Baur, 2010) and can modulate cell survival by regulating the transcriptional activities of p53 (Luo et al., 2000), NF-κB (Yeung et al., 2004), FOXO proteins (Brunet et al., 2004; Motta et al., 2004), and p300 (Bouras et al., 2005).

An association between SIRT1 and MS was suggested by the work of Shindler et al. (2010) who demonstrated resveratrol, a natural plant compound currently being investigated for use in the treatment of diseases including cancer, was neuroprotective in MS patients. Further work by Nimmagadda et al. (2013) showed the mechanism for the immunomodulatory and neuroprotective effects of resveratrol involved the activation of SIRT1.

Because little was known about the changes that occur in SIRT1 expression or in the acetylation and methylation of histones in the PBMC and T cells from MS patients, the investigations reported herein where undertaken. The observations provided herein elucidated the relationship between SIRT1 and RRMS in subjects afflicted with the disease, and form the basis of the invention. Based on the nexus between SIRT1 expression and RRMS, the additional studies on other biomarkers were carried out, leading to the further discovery of a relationship between levels of expression of RGC-32, FasL and IL-21 and RRMS. The present invention provides methods for determining the status of relapse in subjects having RRMS and to predicting whether a subject having RRMS will respond to treatment using the drug glatiramer acetate (GA).

In a first embodiment, the invention is thus generally drawn to methods for determining whether a subject having relapsing-remitting multiple sclerosis (RRMS) is undergoing relapse of the disease by monitoring levels of mRNA expression of certain biomarkers. In particular, the invention is drawn to methods for determining whether a subject having relapsing-remitting multiple sclerosis (RRMS) is undergoing relapse of the disease, comprising (i) determining mRNA expression levels for one or more biomarkers selected from the group consisting of SIRT1, RGC-32, FasL and IL-21 in a population of cells, (ii) determining mRNA expression levels for L13 in the same population of cells, and (iii) calculating a ratio of biomarker mRNA expression to L13 mRNA expression, wherein when the biomarker is SIRT1 and the SIRT1/L13 ratio is <3.06±10%, the subject is determined to be undergoing relapse, wherein when the biomarker is RGC-32 and the RGC-32/L13 ratio is <1.27±10%, the subject is determined to be undergoing relapse, wherein when the biomarker is FasL and the FasL/L13 ratio is <52.6±10%, the subject is determined to be undergoing relapse, and wherein when the biomarker is IL-21 and the IL-21/L13 ratio is >16.9±10%, the subject is determined to be undergoing relapse.

In this embodiment, the range encompassing the noted SIRT1/L13 ratio can also be about ±9%, ±8%, ±7%, ±6%, ±5%, ±4%, ±3%, ±2%, or ±1%. In certain preferred aspects, the SIRT1/L13 ratio is about <3.01, <3.02, <3.03, <3.04, <3.05, <3.06, <3.07, <3.08, <3.09, <3.10, <3.11, or <3.12.

In this embodiment, the range encompassing the noted RGC-32/L13 ratio can also be about ±9%, ±8%, ±7%, ±6%, ±5%, ±4%, ±3%, ±2%, or ±1%. In certain preferred aspects, the RGC-32/L13 ratio is about <1.22, <1.23, <1.24, <1.25, <1.26, <1.27, <1.28, <1.29, <1.30, <1.31, <1.32, or <1.33.

In this embodiment, the range encompassing the noted FasL/L13 ratio can also be about ±9%, ±8%, ±7%, ±6%, ±5%, ±4%, ±3%, ±2%, or ±1%. In certain preferred aspects, the FasL/L13 ratio is about <52.55, <52.56, <52.57, <52.58, <52.59, <52.6, <52.61, <52.62, <52.63, <52.64, <52.65 or <52.66.

In this embodiment, the range encompassing the noted IL-21/L13 ratio can also be about ±9%, ±8%, ±7%, ±6%, ±5%, ±4%, ±3%, ±2%, or ±1%. In certain preferred aspects, the IL-21/L13 ratio is about >16.85, >16.86, >16.87, >16.88, >16.89, >16.9, >16.91, >16.92, >16.93, >16.94, >16.95, or >16.96.

In the various aspects of this embodiment, mRNA expression levels for one, two, three or all of the four biomarkers is determined.

As indicated by this embodiment of the invention, the data obtained from the method will indicate whether the subject is undergoing relapse. Based on this information, a physician can determine the best course of new or continuing treatment for the subject. Thus, when the method indicates that the subject is undergoing relapse, the method can further comprise administering a therapeutically effective amount of a treatment for RRMS to the subject. The treatment may be, for example, glatiramer acetate (GA). Other suitable treatments for RRMS include, but are not limited to, beta-interferons, teriflunomide, fingolimod, dimethyl fumarate, and natalizumab.

In a second embodiment, the invention is generally drawn to methods for determining whether a subject having relapsing-remitting multiple sclerosis (RRMS) is undergoing relapse of the disease by monitoring levels of protein expression of certain biomarkers. In particular, the invention is drawn to methods for determining whether a subject having relapsing-remitting multiple sclerosis (RRMS) is undergoing relapse of the disease, comprising (i) determining protein expression levels for SIRT1 in a population of cells, (ii) determining protein expression levels for L13 in the same population of cells, and (iii) calculating a ratio of SIRT1 protein expression to L13 protein expression, wherein when the SIRT1/L13 ratio is <0.645±10%, the subject is determined to be undergoing relapse.

In this embodiment, the range encompassing the noted SIRT1/L13 ratio can also be about ±4%, ±3%, ±2%, or ±1%. In certain preferred aspects, the SIRT1/L13 ratio is about <0.61, <0.62, <0.63, <0.64, <0.645, <0.65, <0.66, <0.67, <0.68, <0.69, or <0.70.

As indicated by this embodiment of the invention, the data obtained from the method will indicate whether the subject is undergoing relapse. Based on this information, a physician can determine the best course of new or continuing treatment for the subject. Thus, when the method indicates that the subject is undergoing relapse, the method can further comprise administering a therapeutically effective amount of a treatment for RRMS to the subject. The treatment may be, for example, glatiramer acetate (GA). Other suitable treatments for RRMS include, but are not limited to, beta-interferons, teriflunomide, fingolimod, dimethyl fumarate, and natalizumab.

In a third embodiment, the invention is generally drawn to methods for determining whether a subject having relapsing-remitting multiple sclerosis (RRMS) will respond to treatment with glatiramer acetate (GA). In particular, the invention is drawn to methods for determining whether a subject having relapsing-remitting multiple sclerosis (RRMS) will respond to treatment with GA, comprising (i) determining mRNA expression levels for one or more biomarkers selected from the group consisting of SIRT1, RGC-32, FasL and IL-21 in a population of cells, (ii) determining mRNA expression levels for L13 in the same population of cells, and (iii) calculating a ratio of biomarker mRNA expression to L13 mRNA expression, wherein when the biomarker is SIRT1 and the SIRT1/L13 ratio is >4.33±10%, it is determined that the subject will respond to treatment with GA, wherein when the biomarker is RGC-32 and the RGC-32/L13 ratio is >2.52±10%, it is determined that the subject will respond to treatment with GA, wherein when the biomarker is FasL and the FasL/L13 ratio is >85.4±10%, it is determined that the subject will respond to treatment with GA, and wherein when the biomarker is IL-21 and the IL-21/L13 ratio is <11.9±10%, it is determined that the subject will respond to treatment with GA.

In this embodiment, the range encompassing the noted SIRT1/L13 ratio can also be about ±9%, ±8%, ±7%, ±6%, ±5%, ±4%, ±3%, ±2%, or ±1%. In certain preferred aspects, the SIRT1/L13 ratio is about >4.33, >4.27, >4.28, >4.29, >4.3, >4.31, >4.32, >4.33, >4.34, >4.35, >4.36, >4.37, or >4.38.

In this embodiment, the range encompassing the noted RGC-32/L13 ratio can also be about ±9%, ±8%, ±7%, ±6%, ±5%, ±4%, ±3%, ±2%, or ±1%. In certain preferred aspects, the RGC-32/L13 ratio is about >2.47, >2.48, >2.49, >2.50, >2.51, >2.52, >2.53, >2.54, >2.55, >2.56, >2.57, or >2.58.

In this embodiment, the range encompassing the noted FasL/L13 ratio can also be about ±9%, ±8%, ±7%, ±6%, ±5%, ±4%, ±3%, ±2%, or ±1%. In certain preferred aspects, the FasL/L13 ratio is about >85.35, >85.36, >85.37, >85.38, >85.39, >85.4, >85.41, >85.42, >85.43, >85.44, >85.45, or >85.46.

In this embodiment, the range encompassing the noted IL-21/L13 ratio can also be about ±9%, ±8%, ±7%, ±6%, ±5%, ±4%, ±3%, ±2%, or ±1%. In certain preferred aspects, the IL-21/L13 ratio is about <11.85, <11.86, <11.87, <11.88, <11.89, <11.9, <11.91, <11.92, <11.93, <11.94, <11.95, or <11.96.

In the various aspects of this embodiment, mRNA expression levels for one, two, three or all of the four biomarkers is determined.

As indicated by this embodiment of the invention, the data obtained from the method will indicate whether a subject having relapsing-remitting multiple sclerosis (RRMS) will respond to treatment with glatiramer acetate GA. Based on this information, a physician can determine the best course of new or continuing treatment for the subject. Thus, when it is determined that the subject will respond to treatment with GA, the method further comprises administering a therapeutically effective amount of GA to the subject. When it is determined that the subject will not respond to treatment with GA, the method further comprises administering a therapeutically effective amount of another, non-GA treatment suitable for RRMS including, but not limited to, beta-interferons, teriflunomide, fingolimod, dimethyl fumarate, and natalizumab.

In each of the embodiments and aspects of the invention, the population of cells may be, but is not limited to, peripheral blood mononuclear cells (PBMCs), CD4+ T cells, CD8+ T cells, MAB328+ cells, GFAP+ cells, leukocytes, monocytes, glial cells, dendritic cells, and neurons.

In each of the embodiments and aspects of the invention, the methods may include one or more of the following steps: (i) obtaining a biological sample from the subject, such as a sample of cells or a blood sample, (ii) isolating a selected cell type from a biological sample from the subject, (iii) isolating polynucleotides from a selected cell type from a biological sample from the subject, (iv) isolating polypeptides from a selected cell type from a biological sample from the subject, (v) amplifying mRNA from isolated polynucleotides from a selected cell type from a biological sample from the subject, (vi) preparing cDNA from isolated polynucleotides from a selected cell type from a biological sample from the subject, (vii) determining the level of mRNA expression for a selected biomarker in a selected cell type from a biological sample from the subject, (viii) determining the level of cDNA expression for a selected biomarker in a selected cell type from a biological sample from the subject, (ix) determining the level of protein expression for a selected biomarker in a selected cell type from a biological sample from the subject, (x) amplifying L13 mRNA from isolated polynucleotides from a selected cell type from a biological sample from the subject, (xi) amplifying L13 cDNA from isolated polynucleotides from a selected cell type from a biological sample from the subject, (xii) determining the level of L13 mRNA expression in a selected cell type from a biological sample from the subject, (xiii) determining the level of L13 cDNA expression in a selected cell type from a biological sample from the subject, and (xiv) determining the level of L13 protein expression in a selected cell type from a biological sample from the subject.

In each of the embodiments and aspects of the invention, the subject is a human, a non-human primate, bird, horse, cow, goat, sheep, a companion animal, such as a dog, cat or rodent, or other mammal.

III. Examples

Materials and Methods

Brain Tissue

Frozen brain tissue specimens acquired at autopsy from six patients with a definitive diagnosis of MS were obtained from the Human Brain and Spinal Fluid Resource Center, Veterans Affairs West Los Angeles Health Care Center. Active lesions contained abundant infiltrates consisting of T cells and macrophages, with detectable myelin degradation products. Inflammation was restricted to the lesion margins in chronic active lesions. Regions of normal-appearing white matter (NAWM) and normal-appearing gray matter lesions (NAGM) that lacked macroscopic or histological evidence of demyelination were also used. The samples were derived from patients between the ages of 38 and 51, with a mean age of 47. Four healthy control brain samples from patients between the ages of 36-72, with a mean age of 49, were obtained from the Cooperative Human Tissue Network, Charlottesville, Va.

Immunohistochemical Staining for SIRT1 and HDAC3

Immunohistochemical staining of brains from MS patients was performed as previously described (Cudrici et al., 2007). The air-dried cryostat brain sections (4-6 μm) were fixed for 10 min in acetone containing 0.3% $H_2O_2$ to remove endogenous peroxidase. Tissue sections were blocked for 10 min with 2.5% horse serum, then incubated overnight at 4° C. with rabbit anti-SIRT1 (Cell Signaling, Danvers, Mass.) or mouse monoclonal anti-SIRT1 (Active Motif, Carlsbad) as previously described (Fosbrink et al., 2005). For HDAC3 immunolocalization, a mouse monoclonal anti-HDAC3 (BD Biosciences, San Jose, Calif.) was used. For phosphor-SIRT1, an antibody targeting serine 47 (Cell Signaling) was used and for phosphor-HDAC3, an antibody targeting serine 424 (Assay Biotech, Sunnivale, Calif.) was used. The slides were washed three times for 3 min each with PBS, pH 7.4, and then incubated with biotinylated pan-specific universal antibody (Vector Labs, Burlingame, Calif.), followed by streptavidin/peroxidase complex reagent (Vector Labs). Specific reactions were developed using NovaRED (Vector Labs) as the substrate; slides were then counterstained with Harris's hematoxylin (Sigma, St. Louis, Mo.) and mounted with permanent mount. For CD4 and CD68 detection, brain cryosections were processed as described above and then incubated with mouse monoclonal anti-CD4 antibody (NovoCastra, Newcastle upon Tyne, U.K.), diluted 1/50, for 2 h at room temperature (RT) or with mouse monoclonal CD68 (Dako, Carpenteria, Calif.), diluted 1/200, for 1 h at RT. The sections were washed with PBS, pH 7.4, and then incubated for 1 h at RT with HRP-conjugated goat anti-mouse IgG (Jackson Immunoresearch, West Grove, Pa.). Specific reactions were again developed using NovaRED. The immunostained samples were analyzed by two independent scientists.

Double-Staining Immunohistochemistry

Frozen sections of brains from patients with MS were double-stained for SIRT1 and CD3, CD4, CD68, MAB328, or GFAP as previously described (Tegla et al., 2013). Cryosections were initially processed for SIRT1 immunostaining as described above, and the reactions developed with NovaRED. Then slides were incubated with anti-CD4 mouse monoclonal antibody (NovaCastra), diluted 1/50 or with mouse monoclonal antibody anti-CD68 (Dako) was followed by alkaline phosphatase-conjugated goat anti-mouse (Sigma), diluted 1/400. The reaction was developed using a Vector alkaline phosphatase substrate kit III (Vector Labs). Similar reactions were performed for oligodendrocytes using a monoclonal antibody against oligodendrocytes/myelin (MAB328, Chemicon, Temecula, Calif.). For the double staining GFAP/SIRT1 the sections were first incubated with mouse monoclonal anti-GFAP (Dako), diluted 1/1000 ON at 4° C. The slides were washed several times in PBS and reacted with goat anti-mouse antibody (Santa Cruz Biotech) for 1 h at RT. The slides were then exposed to NovaRED then exposed to the rabbit IgG anti-SIRT1 followed by alkaline phosphatase conjugated anti-rabbit IgG (Vector Labs). The reaction was developed using a Vector alkaline phosphatase substrate kit III (Vector Labs). Control sections were prepared by immunostaining without the primary antibody or by using control isotype IgG instead of the primary antibody. The immunostained slides were independently evaluated by two investigators.

MS Patients and Controls 29 patients with relapsing-remitting MS (15 patients with stable disease and 14 with relapses) were enrolled in the study. The criteria for inclusion of MS patients in the study were: (i) age 18 to 65 years; (ii) fulfillment of McDonald criteria for definite MS (McDonald et al., 2001; Polman et al., 2005); (iii) relapsing-remitting course; (iv) having newly diagnosed MS, or MS not treated with currently used immunomodulatory drugs (interferon-β or glatiramer acetate) for 3 months prior to study entry; (v) no exacerbations in the 4 weeks before the study; (vi) no i.v. or p.o. steroids for 4 weeks prior to study enrollment; (vii) no treatment with Tysabri, Gilenya, Tecfidera, mitoxantrone, cyclophosphamide, or investigational drugs during the past year; and (viii) a disability score of 0-5.5, as defined by the expanded disability status scale (EDSS) (Kurtzke, 1983). Exclusion criteria for MS patients were: (i) a history of autoimmune disorders, vascular disease, or active acute or chronic infections; (ii) use of antibiotics in the last 30 days; (iii) a history of intracranial or intraspinal tumor or metabolic myelopathy; or (iv) a history of alcohol or drug abuse. Fifteen healthy, age-, gender-, and race-matched healthy controls were also enrolled in the study. Exclusion criteria for controls were: the presence of (i) overt acute or chronic disease(s) or (ii) other autoimmune disease(s).

Collection of PBMCs, Total RNA Purification, and cDNA Synthesis

PBMCs were collected using BD Vacutainer CPT tubes (Becton Dickinson, Franklin Lakes, N.J.). The mononuclear cells were isolated from fresh blood as previously described (Tegla et al., 2013). RNA isolation and cell lysate preparation for protein analysis were performed the same day (Niculescu et al., 1997). Total RNA was purified using the RNeasy Mini Kit (Qiagen, Santa Clarita, Calif.) according to the manufacturer's instructions. RNA (0.5 µg per sample) was mixed with RT buffer, dNTP, and oligo-dT primer (Invitrogen). RNA was denatured by incubation at 65° C. for 5 min. The reverse transcriptase (Promega) and RNase inhibitor (Invitrogen) were then added, and the reaction mixture was incubated at 37° C. for 1 h. The reaction was terminated by incubating the mixture at 95° C. for 5 min (Tegla et al., 2013).

Real-Time PCR

Real-time PCR was performed using a StepOne real-time PCR system (Applied Biosystems, Foster City, Calif.). The primers for the genes investigated were designed and synthesized by IDT (Coralville, Iowa) (Table 1) and used in conjunction with LightCycler FastStart SYBR Green Master (Roche) according to the manufacturer's protocol.

TABLE 1

Primers used for Real-Time PCR

| Gene Symbol | Primer Sequence | SEQ ID NO: | Product (bp) |
|---|---|---|---|
| SIRT1 | For: 5'-TGGCAAAGGA GCAGATTAGTAG-3' | 1 | 159 |
|  | Rev: 5'-GGCATGTCCC ACTATCACTGT-3' | 2 |  |
| HDAC3 | For: 5'-CATGCACCTA GTGTCCAGATTC-3' | 3 | 182 |
|  | Rev: 5'-CACTCTTAAA TCTCCACATCGC-3' | 4 |  |
| RGC-32 | For: 5'-AGGAACAGCT TCAGCTTCAG-3' | 5 | 152 |
|  | Rev: 5'-GCTAAAGTTT TGTCAAGATCAGCA-3' | 6 |  |
| FasL | For: 5'-GCCCATTTAA CAGGCAAGTC-3' | 7 | 110 |
|  | Rev: 5'-ATCACAAGGC CACCCTTCTT-3' | 8 |  |
| L13 | For: 5'-CGTGCGTCTG AAGCCTACA-3' | 9 | 227 |
|  | Rev: 5'-GGAGTCCGTG GGTCTTGAG-3' | 10 |  |
| CDC2 | For: 5'-TTTTCAGAGC TTTGGGCACT-3' | 11 | 100 |
|  | Rev.: 5'-AGGCTTCCT GGTTTCCATTT-3' | 12 |  |
| AKT1 | For: 5'-ACGCCAAGGA GATCATGC-3' | 13 | 185 |
|  | Rev.: 5'-CTCCATGCT GTCATCTTGGTC-3' | 14 |  |

Abbreviations:
For, forward primer;
Rev, reverse primer;
Bpp, base pairs;
RGC-32, response gene to complement 32;
FasL, Fas ligand;
SIRT1, Sirtuin 1;
HDAC3, Histone Deacetylase 3;
L13, ribosomal protein L13.

As a negative control for each real-time PCR assay, the same reaction was performed in the absence of cDNA or reverse transcriptase. For each gene, the cycle threshold ($C_T$) values were determined in the exponential phase of the amplification plot and normalized by subtraction of the $C_T$ value for 18S (generating a $\Delta C_T$ value). The results were normalized to L13 ribosomal protein, a housekeeping gene. A standard curve was generated using serial dilutions of qPCR Reference Total cDNA (Clontech, Mountain View, Calif.), and the normalized mRNA value (NRV) was calculated according to the following formula for relative expression of target mRNA: NRV (TarS/L13), where TarS represents the level of mRNA expression of the target gene, and L13 corresponds to that of the amplified L13 mRNA. In some cases, the –fold change in target gene samples, after normalization with the housekeeping gene (18S), was calculated using the $2^{-\Delta\Delta C_T}$ value, where $\Delta\Delta C_T = \Delta C_T$ (sample)–$\Delta C_T$ (control) and $\Delta CT$ is the $C_T$ value of target gene normalized to the $C_T$ value of the housekeeping gene (Tegla et al., 2013).

RGC-32 Silencing and Transfection of Cells

Transfection of PBMCs:

PBMCs were plated in RPMI-10% FBS in 12-well plates 24 h prior to viral infection. After 24 h, the medium from the plate wells was removed and replaced with 1 ml of polybrene/RPMI-10% FBS medium mixture per well. Cells were then infected by adding the RGC-32 shRNA lentiviral particles (Santa Cruz Biotech) or control lentiviral particles (Santa Cruz Biotech) to the culture medium overnight, as previously described (Tegla et al., 2013). The next day, the culture medium was removed and replaced with 1 ml of RPMI-FCS 10%, and after 24 h, the transfected cells were analyzed for the expression of RGC-32, SIRT1, and L13 mRNA by real-time PCR as described above.

Annexin V Assay:

PBMCs and Jurkat cells were plated in RPMI-10% FBS in 12-well plates 24 h prior to Annexin V FITC FACS analysis. Some of the cells were treated with sirtinol (200 µM) and the binding of Annexin V-FITC to cells was compared with that of cells exposed to vehicle (DMSO) only. Annexin V assay was performed according to manufacturer instructions (BD Biosciences) and only Annexin V FITC positive, propidium iodide negative cells were used in the evaluations since they are reflecting early apoptosis.

Western Blotting

Western blotting was performed as previously described (Rus et al., 1996a; Rus et al., 1996b). PBMC were washed with PBS, then lysed in a buffer consisting of 10 mM Tris-HCl (pH 7.4), 1 mM EDTA, 1 mM EGTA, 1 mM NaF, 20 mM $Na_4P_2O_7$, 1% Triton X-100, 0.1% SDS, 100 mM NaCl, 10% glycerol, 0.5% sodium deoxycholate, 1 mM $Na_3VO_4$, and complete mini protease inhibitor mixture (Roche Applied Science, Indianapolis, Ind.), which was added just prior to use. Protein concentrations were determined using a BCA protein assay kit (Pierce, Rockford, Ill.). Lysates (30 µg of protein) were fractionated on 10% gradient SDS-polyacrylamide gels and transferred to nitrocellulose membranes (Millipore, Bedford, Mass.). The following primary antibodies were used: rabbit IgG anti H3K9ac (Cell Signaling, Danvers Mass.) and mouse monoclonal anti-SIRT1 and rabbit IgG anti-H3K9me2 (both from Active Motif Carlsbad, Calif.). Goat anti-rabbit or goat anti-mouse IgG HRP-conjugated Ab (Santa Cruz Biotech., Santa Cruz, Calif.), as appropriate, was used as a secondary antibody. For detection, enhanced chemiluminescence (ECL, Pierce) was used. Membranes were stripped using Restore Western Blot Stripping Buffer (Pierce) and reprobed for the expression of β-actin (Rockland Immunochemicals, Rockville, Md.). The radiographic band density was measured using UN-SCAN-IT software (Silk Scientific, Orem, Utah) and results expressed as ratio to β-actin.

Patients Treated with Glatiramer Acetate (GA)

A total of 15 patients with RRMS were enrolled in the study. The patients were recruited from the University of Maryland Multiple Sclerosis Center. The mean age was 40 (range, 22-60), and consisted of 60% females (n=9) and 40% males (n=6). The criteria for inclusion of MS patients in the study were: (i) age 18 to 65 years; (ii) fulfillment of the McDonald criteria for definite MS (McDonald et al., 2001; Polman et al., 2005); (iii) relapsing-remitting course; (iv) having newly diagnosed MS, or MS not treated with currently used immunomodulatory drugs (interferon-β or glatiramer acetate) for 3 months prior to study entry; (v) no exacerbations in the 4 weeks before the study; (vi) no i.v. or p.o. steroids for 4 weeks prior to study enrollment; (vii) no treatment with Tysabri, Gilenya, mitoxantrone, cyclophosphamide, or any investigational drug during the past year; and (viii) a disability score of 0-5.5, as defined by the expanded disability status scale (EDSS) (Kurtzke, 1983). Exclusion criteria for MS patients were: (i) a history of autoimmune disorders, vascular disease, or active acute or chronic infections; (ii) use of antibiotics in the last 30 days; (iii) a history of intracranial or intraspinal tumor or metabolic myelopathy; or (iv) a history of alcohol or drug abuse.

All MS patients received 20 mg of glatiramer acetate (GA) injected subcutaneously every day for 2 years. During this period of 2 years, patients were clinically evaluated and peripheral blood samples were collected at 0, 3, 6, and 12 months at the time of their outpatient visits. Patients with symptoms suggestive of a clinical relapse called the University of Maryland Multiple Sclerosis Center. Clinical relapse was defined as substantial worsening of pre-existing symptoms or appearance of new neurological deficits in the absence of fever or infections lasting more than 24 h. An EDSS evaluation was completed at each visit. Clinical records, consultation reports, and inpatient records were reviewed by a neurologist to ensure that the data obtained were complete. In the case of patients with relapse, the administration of 1 g of Solu-Medrol i.v. for 3 days was used to treat the disease exacerbation. A prednisone taper was also used after i.v. Solu-Medrol in certain cases. In such cases, blood samples were obtained prior to Solu-Medrol treatment. Responders to GA treatment were defined as patients who exhibited 0 or no more than 1 relapse event during the 2 year span following the initiation of GA. Non-responders were defined as patients who exhibited 2 or more relapse events during the 2 year span following the initiation of GA. According to these criteria, the present cohort consisted of 11 responders (mean age 43, range 27-60; 55% female) and 4 non-responders (mean age 31, range 22-36; 75% female).

Statistical Analysis

Comparisons between multiple groups were performed using two-way ANOVA or a two-tailed t-test assuming unequal variances. P values<0.05 were considered significant. Pearson correlation analysis was conducted to examine the association between variables. Statistical analysis was performed using SAS software, version 9.2, or IBM SPSS Statistics software version 22 and GraphPad Prism software version 6. All values are shown as means±SEM and are representative of three experiments unless otherwise noted. Receiver operating characteristic (ROC) curve analysis was used to assess the predictive accuracy of each potential biomarker. The predictive probability of binary outcomes regarding clinical state and response to GA treatment was reported as a C-statistic or Area Under the Curve (AUC, represented as a percentage, with a perfect score being 100% predictability).

Results

Immunohistochemical Localization of SIRT1 and HDAC3 in MS Brain

Since effector T cells migrate into the brain at the time of an MS relapse (Costantino et al., 2008; Martinez-Pasamar et al., 2013), the expression of SIRT1 in MS brains was investigated in relation to that of T cells and macrophages. First, the localization of SIRT1 in 20 areas from 8 patients with MS (Table 2) was examined.

MS brain samples from active lesions contained abundant inflammatory cell infiltrates, consisting of CD4$^+$ and CD8$^+$ T cells as well macrophages. Acute active lesions contained inflammatory cells throughout the entire lesion, whereas the inflammation was restricted to the lesion margins in chronic active lesions (Cudrici et al., 2007). It was found that SIRT1 was expressed in both acute and chronic active lesions (FIGS. 1 and 2, Table 2). SIRT1 was also found to be present on cells in both perivascular (FIG. 1A, B) and parenchymal areas (FIG. 1C). The SIRT1 deposition was confined not only to MS plaques but was also present in areas of NAWM and NAGM. In general, the expression of SIRT1 was higher in the MS plaques than in NAWM and NAGM (Table 2).

Figures 2A, 2B, 2C, 2D:
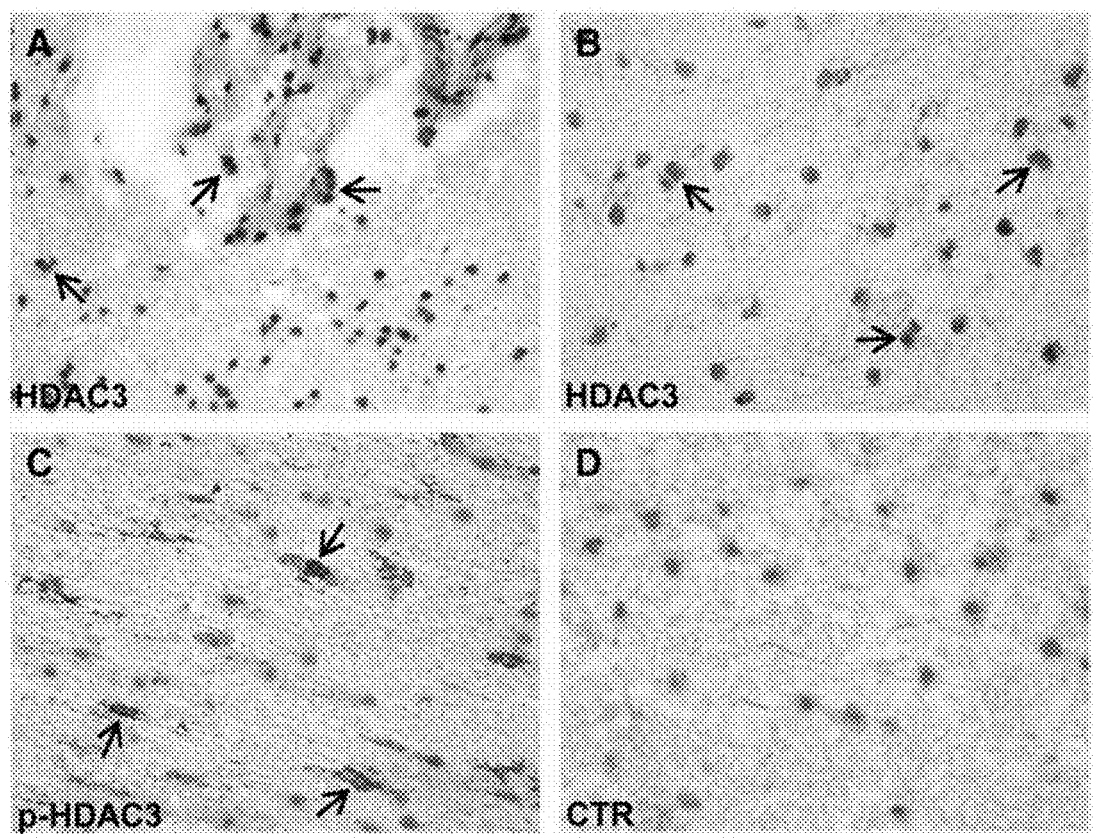
FIGS. 2A-2D. Immunohistochemical staining for HDAC3 and phosphorylated HDAC3 (p-HDAC3) in MS brains. HDAC3 and phosphorylated HDAC3 ("p-HDAC3") were localized in MS brain by immunostaining.

HDAC3 deposition was confined not only to MS plaques but was also present in areas of NAWM and NAGM (Table 2). Expression of HDAC3 was higher in the MS plaques than in NAWM and NAGM. Since both SIRT1 and HDAC3 are regulated by phosphorylation (Sasaki et al., 2008; Zhang et al., 2005), these phosphorylated proteins were localized to MS brains. It was found that SIRT1 phosphorylated (p-SIRT1) at Ser 47 and HDAC3 phosphorylated (p-HDAC3) at Ser 424 were also widely distributed in MS plaques as well as NAGM and NAWM (FIG. 1C, 2C) (Table 2). P-SIRT1 deposits were found only in the nucleus (FIG. 1C), whereas p-HDAC3 was found to be localized both in the cytoplasm and in the nucleus (FIG. 2C).

Co-Localization of SIRT1 with CD4-, CD68-, MAB328-, and GFAP-Positive Cells

Figures 3A, 3B, 3C, 3D, 3E, 3F:
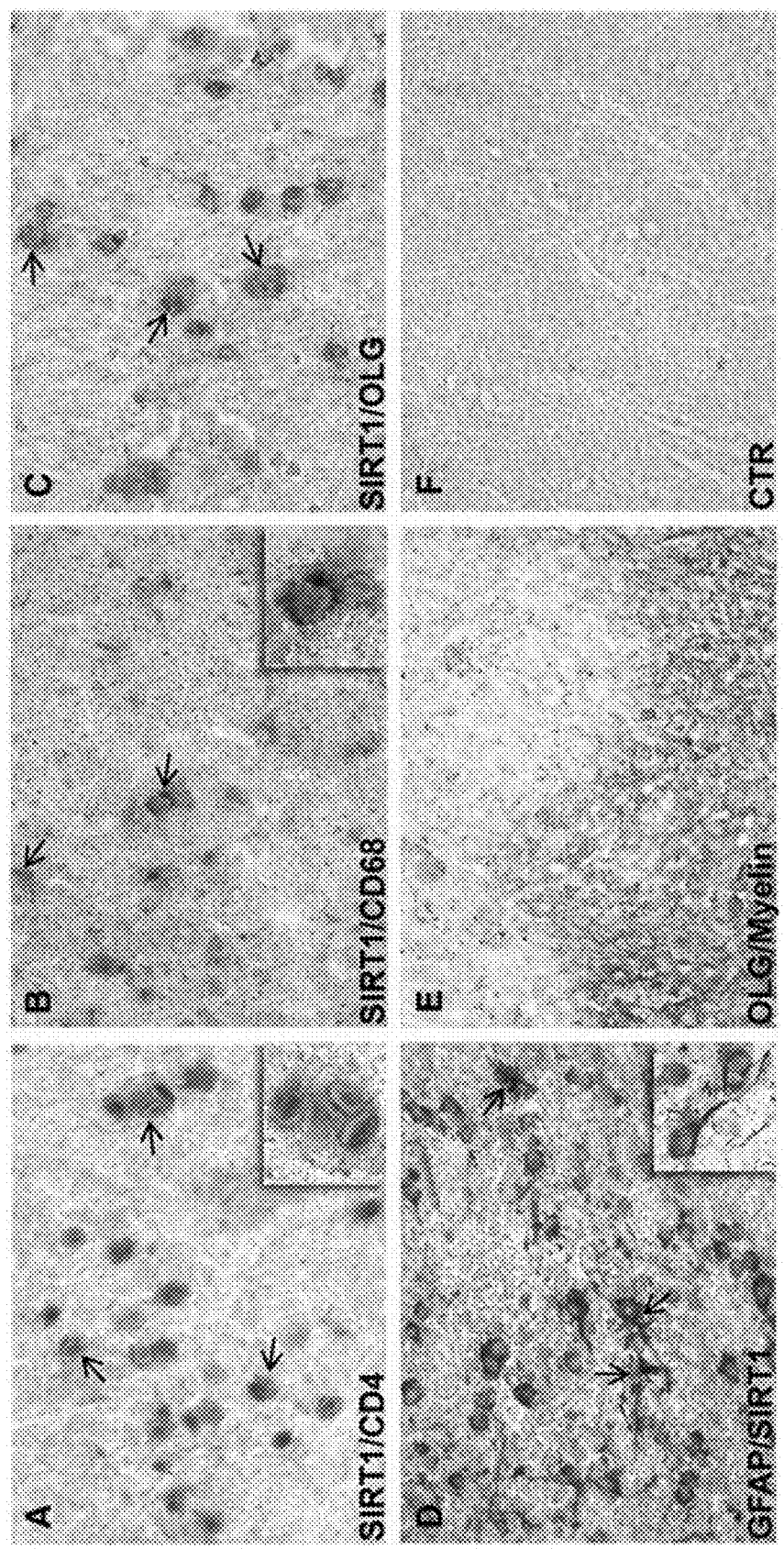
FIGS. 3A-3F. Co-localization of SIRT1 with cells positive for CD4, CD68, GFAP, and MAB328 in MS brains.

To further concentrate efforts on investigating whether CD4- and CD68-positive cells also express SIRT1, double-labeling experiments were carried out using specific antibodies. It was discovered that some of the SIRT1 deposits co-localized with CD4$^+$ cells (FIG. 3A). It was also found that some of the CD68$^+$ cells in MS plaques co-localized with SIRT1 (FIG. 3B). In addition, SIRT1 was present on CD68$^+$ cells that had morphology suggestive of glial cells (data not shown). In addition to CD4- and CD68-positive cells, MAB328 and GFAP-positive cells also co-localized

TABLE 2

Expression of SIRT1, phospho-SIRT1, HDAC3 and phospho-HDAC3 in MS brain.

| Case no. (Age, sex) | Lesion (no.) | Lesion Type | SIRT1 Peri-vascular | SIRT1 Paren-chymal | Phospho-SIRT1 Peri-vascular | Phospho-SIRT1 Paren-chymal | HDAC3 Peri-vascular | HDAC3 Paren-chymal | Phospho-HDAC3 Peri-vascular | Phospho-HDAC3 Paren-chymal |
|---|---|---|---|---|---|---|---|---|---|---|
| 1 (53, F) | Occipital (3) | Chronic active | ++ | ++ | +++ | +++ | +/++ | + | ++ | ++ |
|  |  | NAWM | ++ | ++ | +++ | +++ | +/++ | ++ | ++ | ++ |
|  |  | NAGM | + | ++ | ++/+++ | ++/+++ | ++ | +++ | + | ++ |
|  | Parietal (3) | Chronic active | ++ | ++ | ++/+++ | +++ | ++ | +/++ | ND | ND |
|  |  | NAWM | ++ | +++ | ++/+++ | ++/+++ | +/++ | +++ | +/++ | ++ |
|  |  | NAGM | ++ | ++ | +++ | +++ | + | ++ | +/++ | ++ |
| 2 (68, M) | Parietal (3) | Acute | ++ | +++ | ND | ND | +/++ | ++ | ND | ND |
|  |  | NAWM | ++ | +++ | +++ | +++ | +++ | ++ | ND | ND |
|  |  | NAGM | +/++ | ++ | +++ | +++ | ++ | ++ | + | +++/++ |
| 3 (62, M) | Parietal (3) | Acute | ++ | +++ | ND | ND | ++ | ++/+++ | ++ | ++ |
|  |  | NAWM | +++ | +++ | ND | ND | + | ++ | ++ | ++ |
|  |  | NAGM | + | ++ | ND | ND | + | ++ | ++ | +++ |
| 4 (38, F) | Frontal (3) | Chronic active | + | +/++ | +++ | +++ | ND | ND | ND | ND |
|  |  | NAWM | + | ++ | +++ | +++ | +/++ | ++ | ND | ND |
|  |  | NAGM | + | + | +++ | +++ | + | + | ND | ND |
| 5 (51, F) | Frontal (2) | Chronic active | + | ++ | +++ | ++/+++ | + | ++ | + | ++ |
|  |  | NAGM | + | +/++ | ++ | ++ | ++ | ++ | ND | ND |
| 6 (47, F) | Parietal (3) | Acute | +/++ | +++ | +++ | +++ | + | + | ND | ND |
|  |  | NAWM | +/++ | +++ | +++ | +++ | + | + | ND | ND |
|  |  | NAGM | ++ | ++ | +++ | +++ | +++ | ++ | ND | ND |

Abbreviations used in the table:
F: female;
M: male;
NAWM: normal appearing white matter;
NAGM: normal appearing gray matter;
ND: non-determined;
+ slightly positive;
++ positive;
+++ highly positive.

SIRT1 was not found to be expressed in normal brain, with the exception of rare neurons in the cortex. Controls for the immunoperoxidase reaction using isotype IgG instead of the primary antibody were all negative (FIG. 1D). The expression of HDAC3 in MS brain was also investigated since this protein was previously reported to be expressed by PBMCs of MS patients (Zhang et al., 2011). Like SIRT1, HDAC3 was also found to be present in periventricular and parenchymal areas of MS brains (FIG. 2A, B) (Table 2). The with SIRT1 (FIG. 3C, D), indicating that OLG and astrocytes in MS brains also express SIRT1. Immunoperoxidase reaction controls by replacing primary antibodies with PBS were negative (FIG. 3F).

Expression of SIRT1 and HDAC3 in PBMCs of RR MS Patients and Controls

The expression of SIRT1 and HDAC3 in unstimulated PBMCs was next examined in relation to disease activity.

Figures 4A, 4B, 4C:
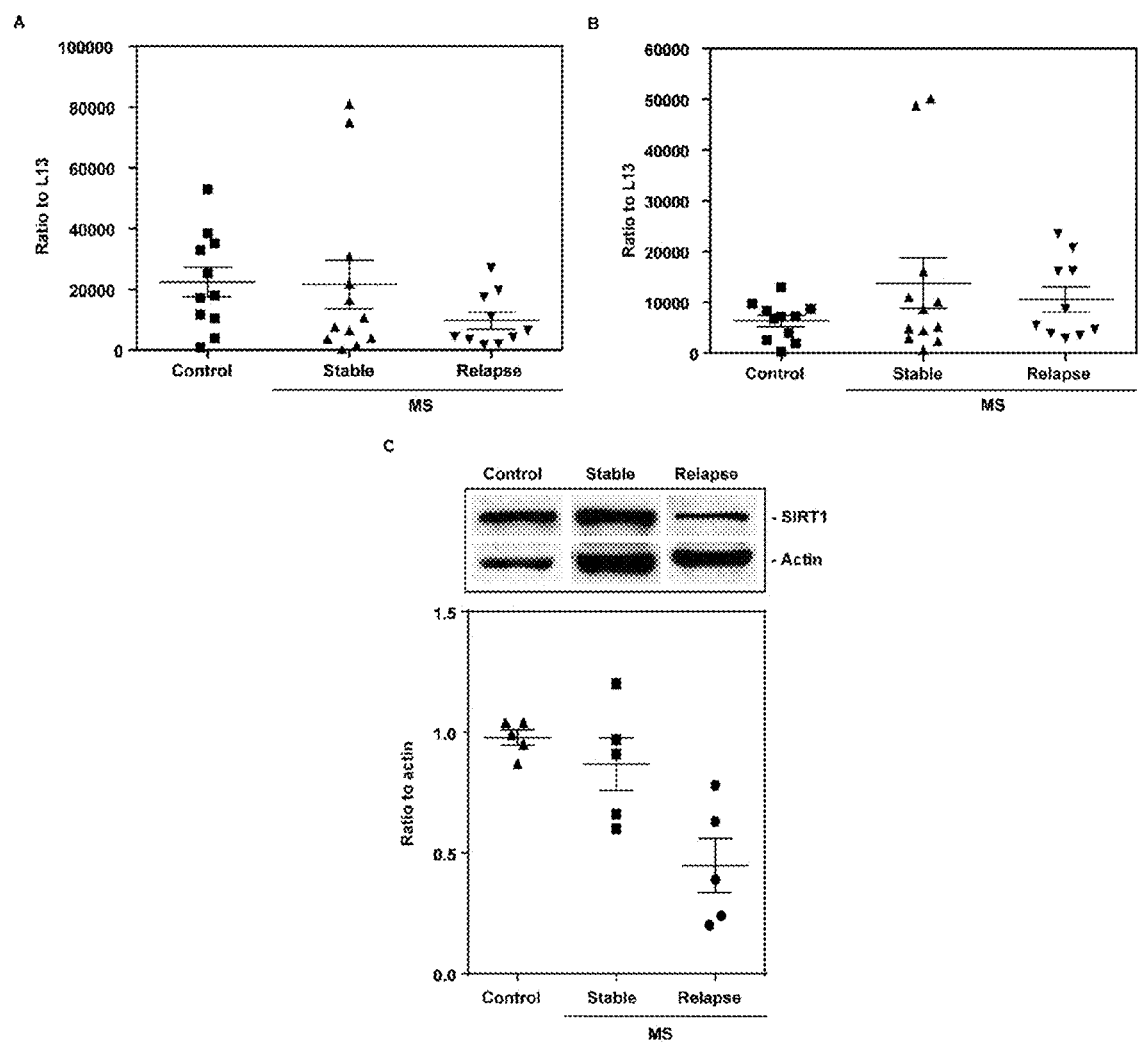
FIGS. 4A-4C. Expression of SIRT1 and HDAC3 in MS patients and controls. The expression of SIRT1 and HDAC3 mRNA was measured by real-time PCR and expressed as a ratio to L13. SIRT1 protein was measured by western blotting.

Expression of SIRT1, HDAC3, and L13 (a housekeeping gene) mRNA was measured by real-time PCR. MS samples were divided into those from stable periods in which no clinical activity was present and those from periods of relapse in which clinical activity was present and had been detected by a neurologist. A statistically significant decrease in SIRT1 mRNA was seen in patients with relapses when compared to controls (p<0.04). Stable relapsing-remitting MS patients had levels of SIRT1 mRNA expression that were similar to those of control subjects (FIG. 4A). Also, HDAC3 mRNA levels were not significantly changed in MS patients when compared to controls (FIG. 4B). SIRT1 protein expression was determined by western blotting, and levels of SIRT1 protein were also found to be significantly decreased in patients with relapses when compared to stable MS patients (p<0.01) and controls (p<0.02) (FIG. 3C). All these data indicate a significant decrease in SIRT1 levels during relapses.

Expression Profile of Histone H3K9Ac and H3K9Me2 in MS Patients

Figures 5A, 5B, 5C, 5D:
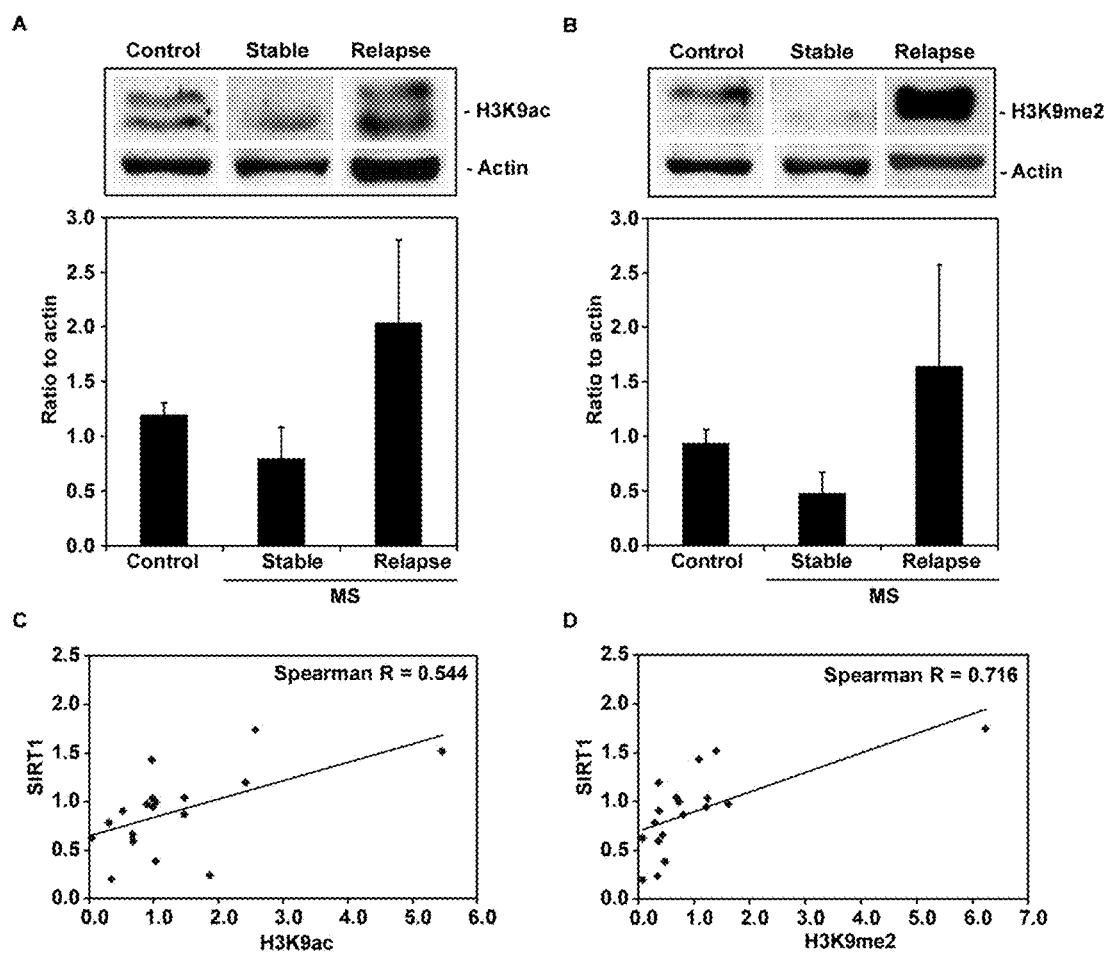
FIGS. 5A-5D. Expression of histone H3K9ac and H3K9me2 in MS patients and controls. Acetylation and methylation of histone H3 at lysine 9 was assessed by western blotting using specific antibodies against H3K9ac and H3K9me2.

Acetylation and methylation of histone H3 at lysine 9 were assessed by western blotting using specific antibodies. Statistically significant higher levels of H3K9ac were found during relapses (p<0.05). A reduction in H3K9 me2 was observed in the PBMCs of stable MS patients when compared to controls, but this difference was not statistically significant. SIRT1 protein levels were positively correlated with expression of H3K9me2 (R=0.716, p=0.0008) and of H3K9ac (R=0.544, p=0.0196) (FIG. 5). These changes are in agreement with the described role of SIRT1 in H3K9 acetylation, with increased acetylation a consequence of the reduced levels of SIRT1 during relapses. SIRT1 is a known regulator of H3K9 methylation and can induce both an increase in methylation and gene silencing (Vaquero et al., 2007; Vaquero et al., 2004).

Effect of RGC-32 Silencing on SIRT1 Expression

Figures 6A, 6B:
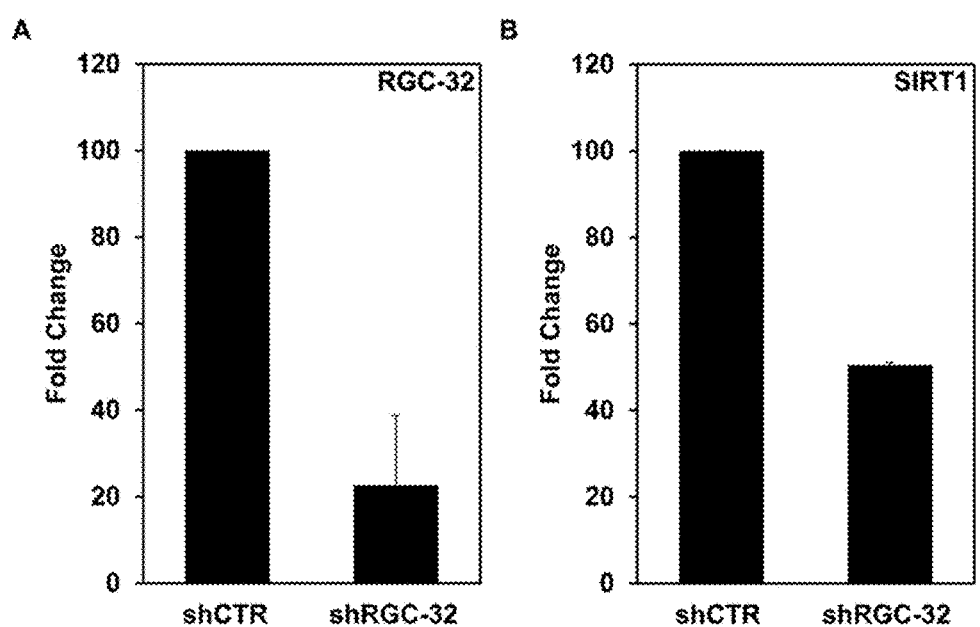
FIGS. 6A-6B. SIRT1 expression is mediated through RGC-32. PBMCs from patients with stable MS were transfected with lentivirus RGC-32 shRNA or shCTR for 48 h. The expression of RGC-32 and SIRT1 mRNA was then determined using real-time PCR.

It was previously shown that SIRT1 expression is regulated by RGC-32 in the SW480 tumor cell line (Vlaicu et al., 2010). To investigate whether RGC-32 is also required for the expression of SIRT1 mRNA in PBMCs, shRNAs targeting RGC-32 was used to silence its expression. PBMCs were transfected with RGC-32 shRNA lentivirus and then tested by real time-PCR to verify their effectiveness in blocking the endogenous expression of RGC-32 mRNA. It was confirmed that RGC-32 shRNA effectively decreased mRNA RGC-32 expression (by 72%) when compared to cells transfected with control shRNA (shCTR) (FIG. 6A). The ability of RGC-32 shRNA to block SIRT1 mRNA expression was then examined. As shown in FIG. 6B, SIRT1 expression was reduced by 50% after RGC-32 silencing, indicating an important role for RGC-32 in SIRT1 expression. These data are in agreement with the reported low levels of RGC-32 in MS patients with relapses (Tegla et al., 2013).

Effect of SIRT1 Inhibition on Apoptosis and FasL Expression

Figures 7A, 7B, 7C:
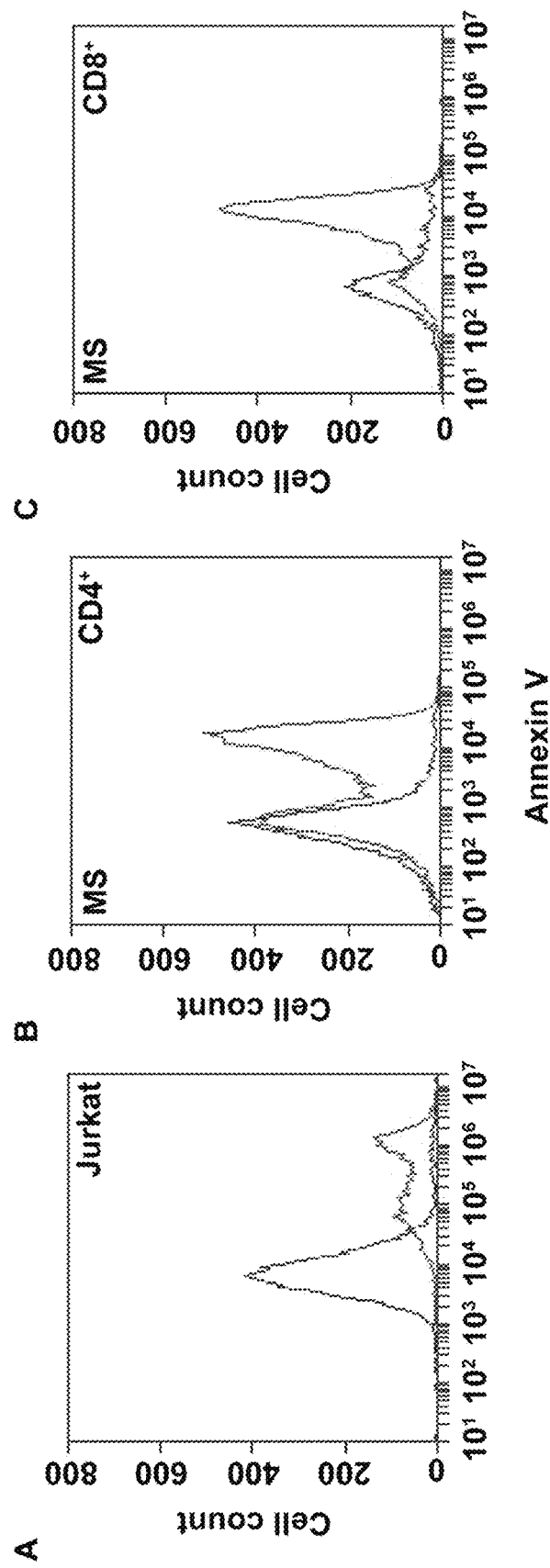
FIGS. 7A-7C. Effect of SIRT1 inhibition on annexin V binding. Jurkat cells (FIG. 7A) and CD4$^+$ (FIG. 7B) and CD8$^+$ (FIG. 7C) T cells from an MS patient were pretreated with the SIRT1 inhibitor sirtinol (200 μM) for 24 h, and Annexin V FITC binding was determined by FACS analysis. Overlay histograms are shown for untreated control cells (left peak in each graph) and sirtinol treated cells (right peak in each graph). As expected, cells that were treated with the vehicle (DMSO) were primarily Annexin V negative. The small number of Annexin V negative cells in control cells represents the basal level of apoptosis. A significant increase in Annexin V binding was found in all studied cells after 24 h of incubation with sirtinol for 24 h.
Figures 8A, 8B, 8C, 8D:
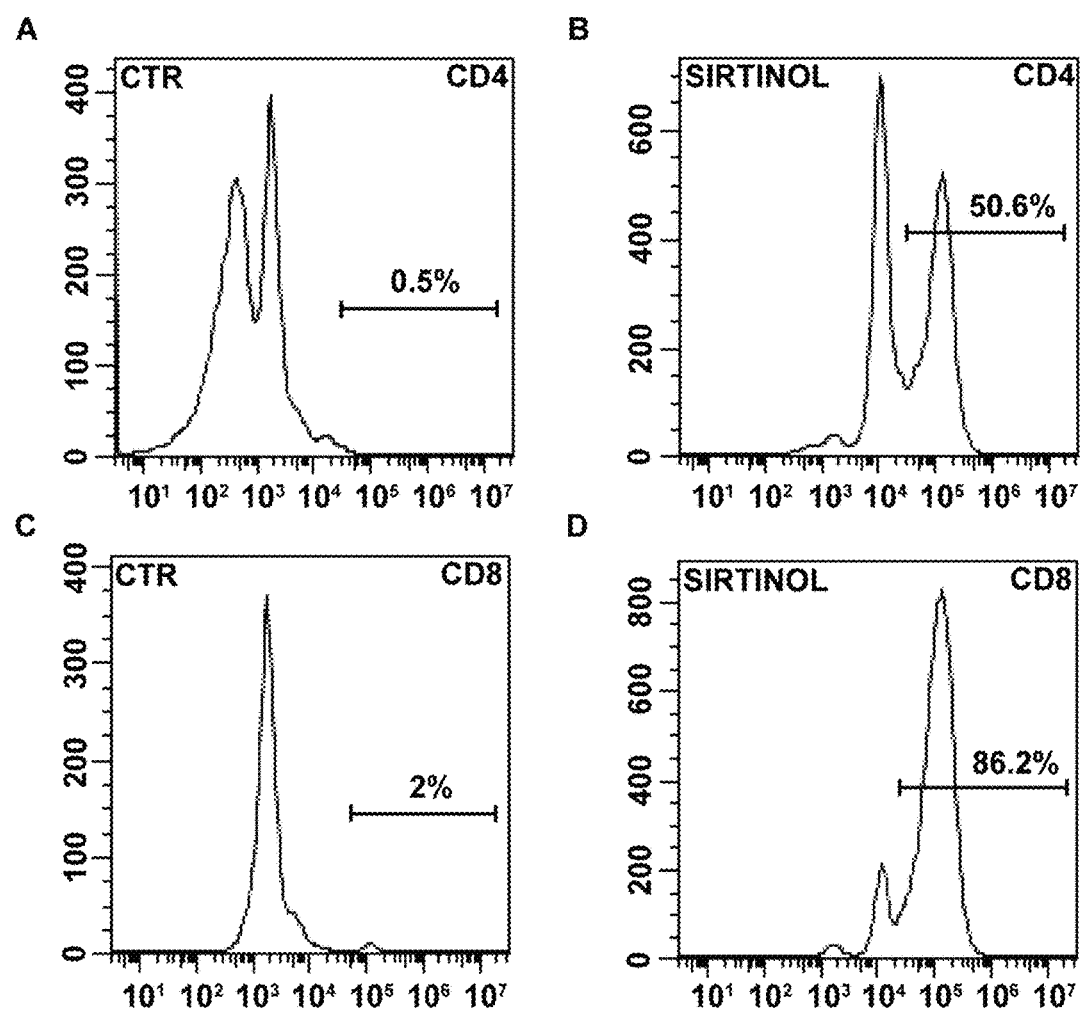
FIGS. 8A-8D. Effect of SIRT 1 inhibition on FasL expression. PBMCs from a stable MS patient (FIG. 8A, FIG. 8C) were pretreated with the SIRT1 inhibitor sirtinol (200 μM) for 24 h (FIG. 8B, FIG. 8D), cultured with CD4$^+$ (FIG. 8B) or CD8$^+$ (FIG. 8D) T cells, and expression of FasL was then determined by FACS analysis. A significant increase in FasL expression in both CD4$^+$ (FIG. 8B) and CD8$^+$ (FIG. 8D) T cells is seen after treatment with the SIRT1 inhibitor.

The effect of sirtinol on apoptosis was investigated in the Jurkat cell line, CD4$^+$, and CD8$^+$ cells. It was found that sirtinol (200 μM) induced binding of Annexin V in 65% of the Jurkat cells (as compared to 6% of the control cells exposed to vehicle DMSO). Similarly, increased apoptosis as seen when CD4 cells (6% in control cells vs 55% in the MS patient) and CD8 cells (22% in control cells vs 81% in the MS patient) were exposed to sirtinol for 24 h (FIG. 7). In order to investigate the effect of SIRT1 inhibition on FasL expression, PBMCs from stable MS patients were used. It was found that sirtinol (200 μM) significantly inhibited the expression of SIRT1 mRNA (by 50%, data not shown) and significantly increased FasL expression (FIG. 8), suggesting a role for SIRT1 in the expression of FasL.

Expression of SIRT1 in Responders Vs Non-Responders

Figure 9:
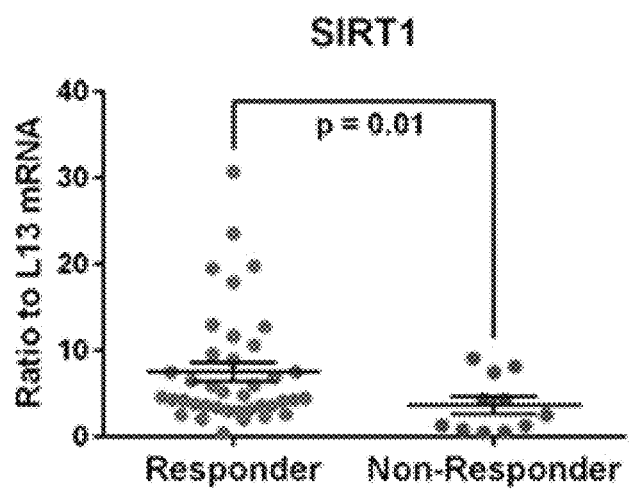
FIG. 9. SIRT1 mRNA in responders and non-responders to Glatiramer Acetate (GA) treatment. SIRT1 mRNA expression was measured in patient PBMCs using real-time qRT-PCR and expressed as a ratio to L13. Significantly higher levels of SIRT1 mRNA were found in responders to glatiramer acetate (GA) compared to non-responders ($p<0.01$).
Figure 10:
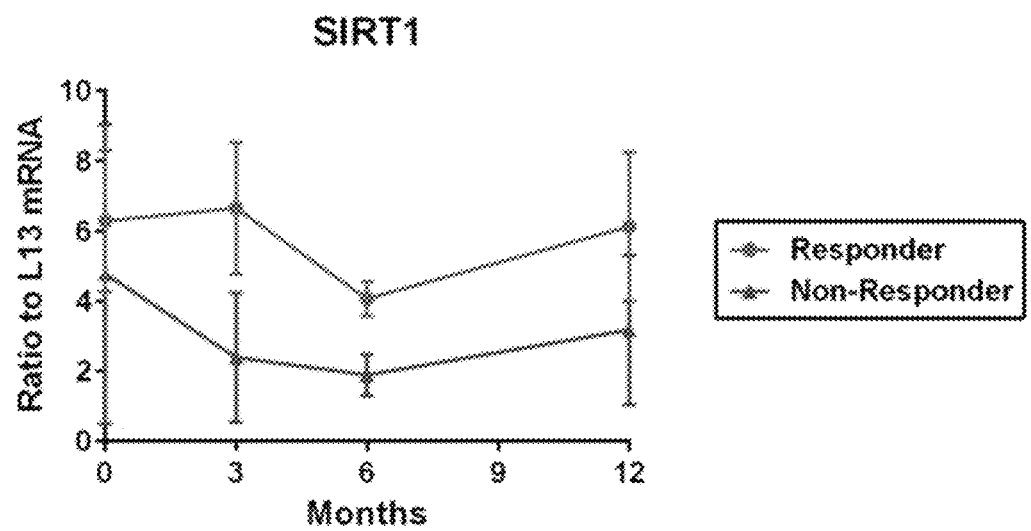
FIG. 10. Time course of SIRT1 mRNA expression in GA-treated MS patients. PBMCs were obtained from patients with RRMS at 0, 3, 6, and 12 months following the initiation of GA treatment. SIRT1 mRNA expression was measured in patient PBMCs using real-time qRT-PCR and expressed as a ratio to L13. Responders to GA showed persistently higher levels of SIRT1 mRNA compared to non-responders over time.

SIRT1 mRNA expression was measured in patients' PBMCs using real-time qRT-PCR and expressed as a ratio to L13. Responders to GA treatment were defined as patients who exhibited 0 or no more than 1 relapse event during the 2 year span following the initiation of GA whereas non-responders exhibited 2 or more relapse events. Significantly higher levels of SIRT1 mRNA were found in responders to GA compared to non-responders (p<0.01) (FIG. 9). Next we examined the time course of SIRT1 mRNA expression in GA-treated MS patients. PBMCs were obtained from patients with RRMS at 0, 3, 6, and 12 months following the initiation of GA treatment. SIRT1 mRNA expression was measured in patients' PBMCs using real-time qRT-PCR and expressed as a ratio to L13. A. Responders to GA showed persistently higher levels of SIRT1 compared to non-responders over time (FIG. 10).

ROC Analysis

Figures 11A, 11B:
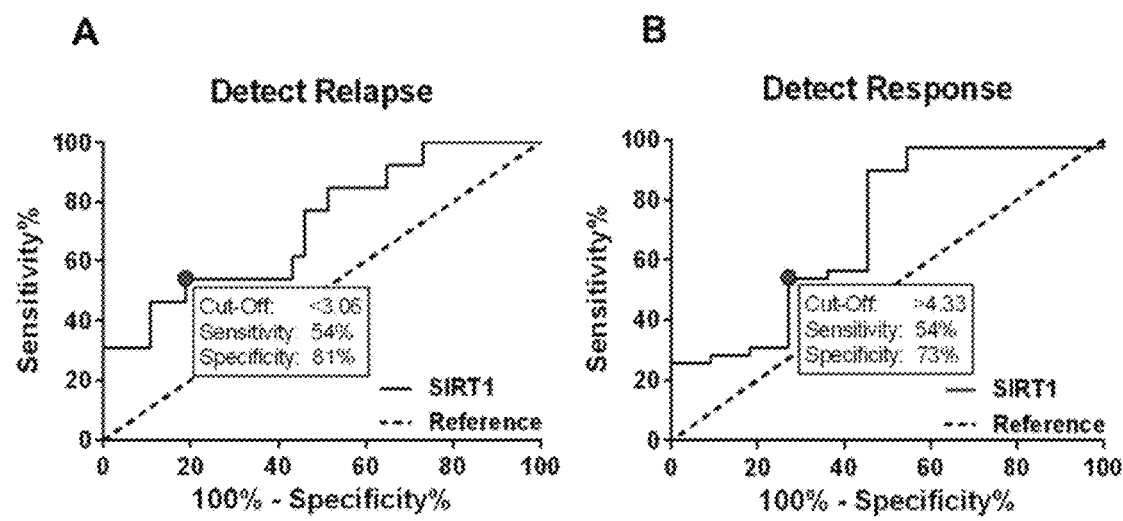
FIGS. 11A-11B. Receiver operating characteristic (ROC) curve analysis to assess the predictive accuracy of SIRT1 mRNA in detecting relapse and response to GA therapy. The probability (C-statistic, or area under the curve (AUC)) of accurately detecting relapse was 72% ($p<0.02$), for response to GA therapy was 70% ($p=0.04$).

ROC analysis was used to assess the predictive accuracy of using SIRT1 mRNA level to detect patient relapse. The probability (C-statistic, or area under the curve (AUC)) of accurately detecting relapse was 72% using SIRT1. In the present cohort, a SIRT1/L13 ratio<3.06 detected patient relapse with specificity of 81% (FIG. 11A).

ROC analysis was used to assess the predictive accuracy of using SIRT1 mRNA level to detect response to GA. The probability (C-statistic, or area under the curve (AUC)) of accurately detecting response to GA was 70% (p=0.04). Using 1SIRT1/L13 ratio>4.33 detected patient response to GA therapy with a specificity of 73% (FIG. 11B).

Figure 12:
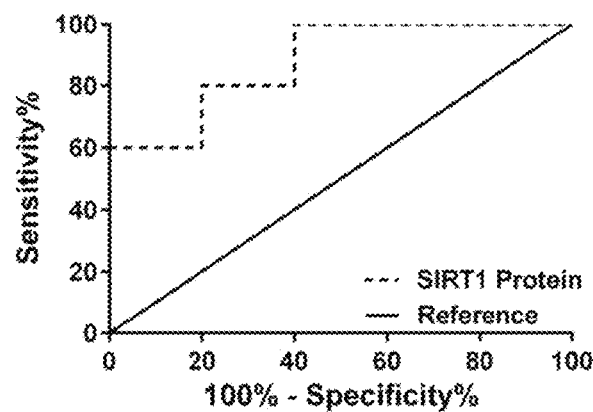
FIG. 12. ROC curve analysis to assess the predictive accuracy of SIRT1 protein in detecting relapse. The probability (C-statistic, or AUC) of accurately detecting relapse was 88% ($p<0.047$). In the present cohort, a SIRT1/L13 ratio<0.645 detected patient relapse with specificity of 80%. AUC, represented as a percentage, with a perfect score being 100% predictability.

ROC curve analysis was also used to assess the predictive accuracy of SIRT1 protein in detecting relapse (FIG. 12). The probability (C-statistic, or AUC) of accurately detecting relapse was 88% using (p<0.047). In the present cohort, a SIRT1/L13 ratio<0.645 detected patient relapse with specificity of 80%.

Expression of RGC-32, FasL, CDC2, AKT, and IL-21 mRNA in Acute MS Relapse

Figures 13A, 13B, 13C, 13D, 13E, 13F:
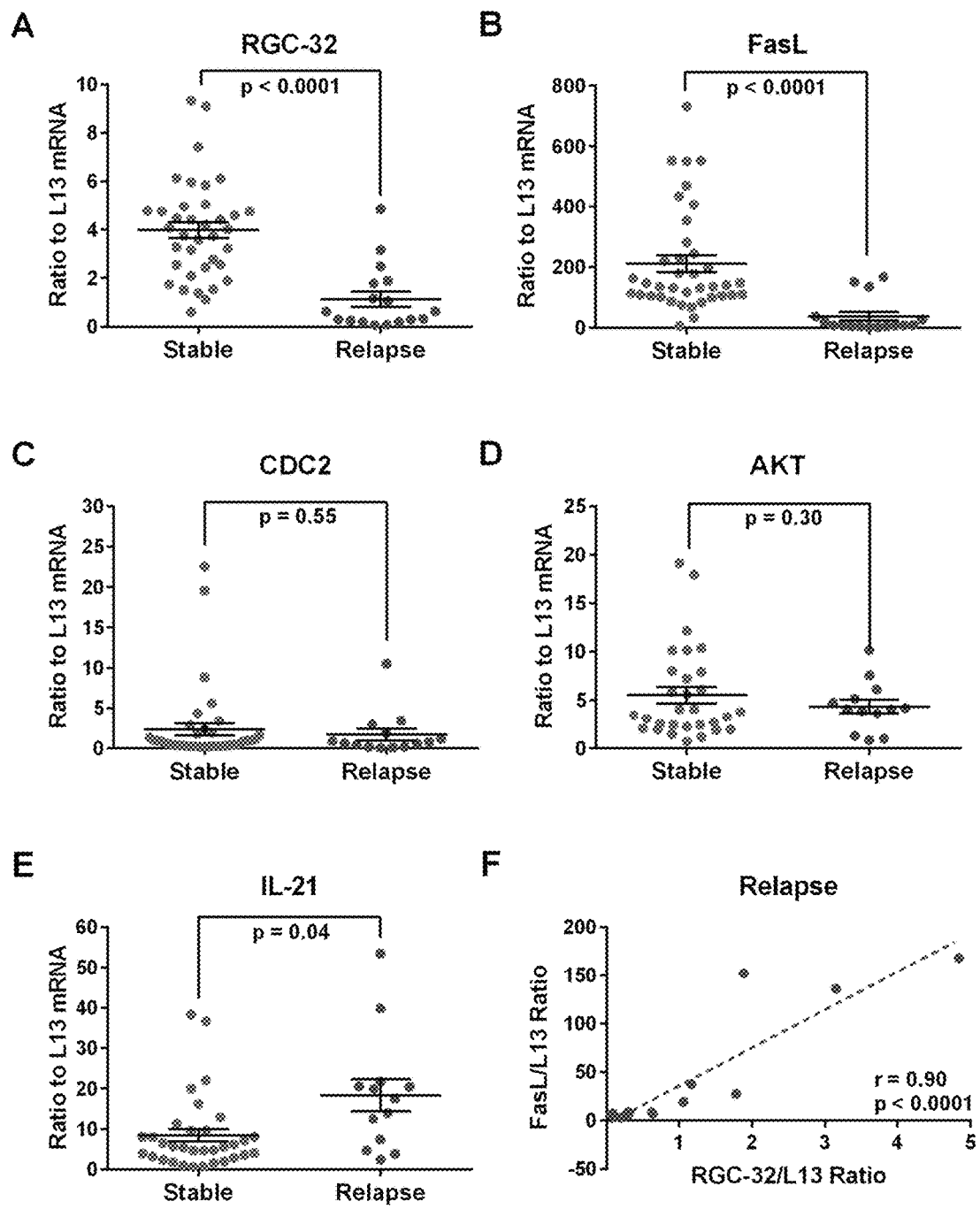
FIGS. 13A-13F. Expression of RGC-32, FasL, CDC2, AKT, and IL-21 mRNA in stable MS patients and patients with acute relapses. Target gene mRNA expression was measured in patient PBMCs using real-time qRT-PCR and expressed as a ratio to L13.

The expression of RGC-32 mRNA in unstimulated PBMCs was examined in relation to disease activity. FasL and CDC2 mRNA expression were also investigated because RGC-32 is known to bind to and regulate CDC2, which in turn has a regulatory effect on FasL expression (Badea et al., 2002; Fosbrink et al., 2009; Torgler et al., 2004). In addition, IL-21 and AKT mRNA expression were investigated as previously described (Tegla et al., 2013). MS patient PBMC samples were categorized into those from stable periods in which no clinical activity was present and those from periods of relapse, in which clinical activity was present and had been detected by a neurologist. Target gene mRNA expression was measured in patient PBMCs using real-time qRT-PCR and expressed as a ratio to L13. Statistically significant lower levels of RGC-32 mRNA were found in MS patients with relapses compared to those who were clinically stable (p<0.0001) (FIG. 13A). Patients with relapses also exhibited significantly lower levels of FasL mRNA compared to stable MS patients (p<0.0001) (FIG. 13B). Levels of CDC2 and AKT mRNA in MS patients with relapses were similar to those in stable patients (FIG. 13C, D). On the other hand, IL-21 mRNA expression was significantly higher in MS patients with relapses compared to stable MS patients (p=0.04) (FIG. 13E). As shown in FIG.

13F, RGC-32 and FasL mRNA expression levels were positively correlated within MS patients during relapses (r=0.90, p<0.0001).

Figures 14A, 14B, 14C, 14D, 14E:
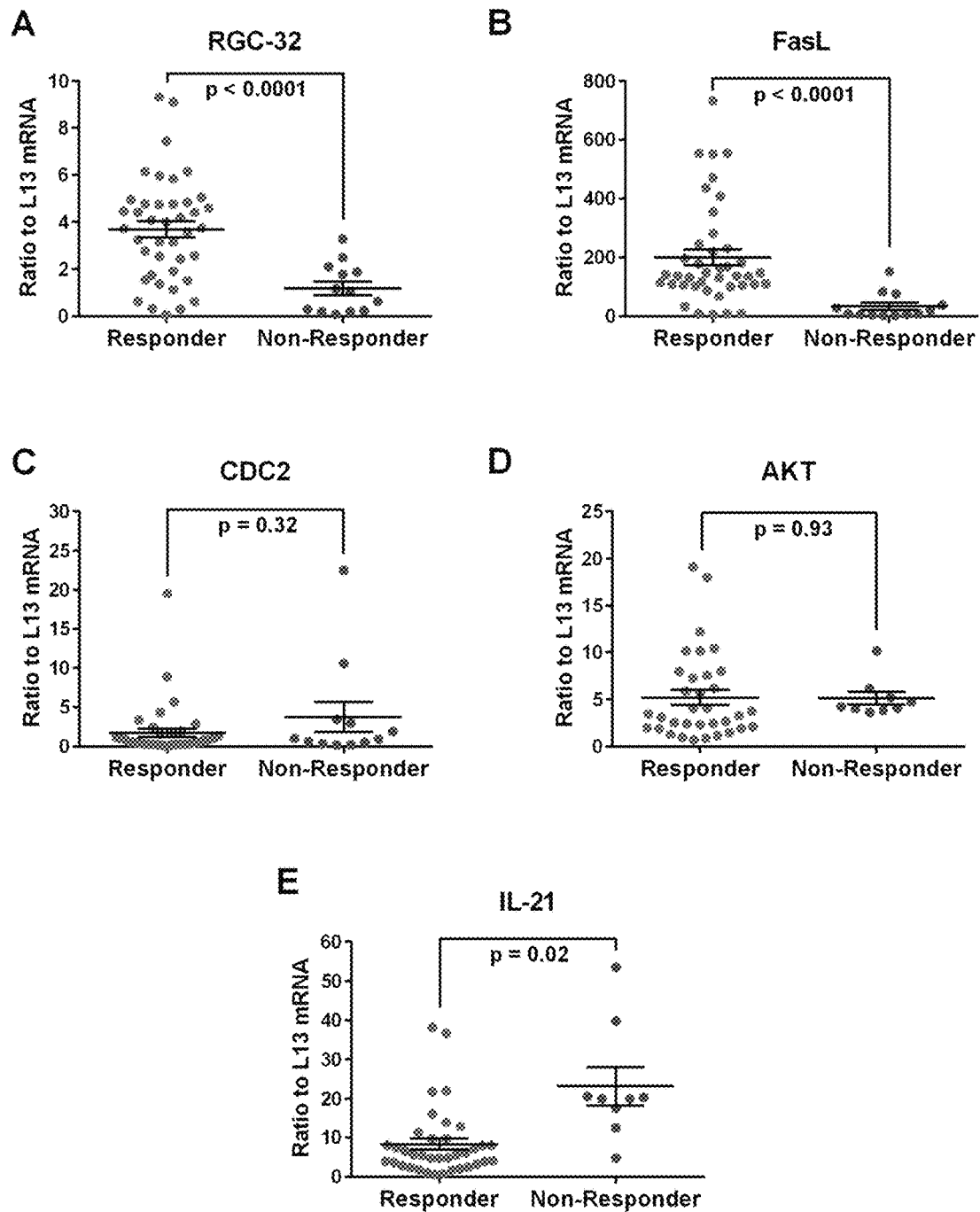
FIGS. 14A-14E. Expression of RGC-32, FasL, CDC2, AKT, and IL-21 mRNA in responders and non-responders to GA treatment. Target gene mRNA expression was measured in patient PBMCs using real-time qRT-PCR and expressed as a ratio to L13.

Expression of RGC-32, FasL, CDC2, AKT, and IL-21 mRNA in Responders Vs. Non-Responders to GA Treatment Since GA is an effective treatment for RRMS, the relationship between RGC-32, FasL, CDC2, AKT, and IL-21 mRNA expression and responsiveness to treatment over time was investigated. Responders to GA treatment were defined as patients who exhibited 0 or no more than 1 relapse event during the 2 year span following the initiation of GA whereas non-responders exhibited 2 or more relapse events. Overall, responders to GA treatment showed significantly higher levels of RGC-32 (p<0.0001) and FasL (p<0.0001) (FIG. 14A, B). No significant change was observed in CDC2 or AKT expression between responders and non-responders (FIG. 14C, D). IL-21 mRNA levels were lower in responders to GA treatment compared to non-responders (p=0.02) (FIG. 14E).

Figures 15A, 15B, 15C:
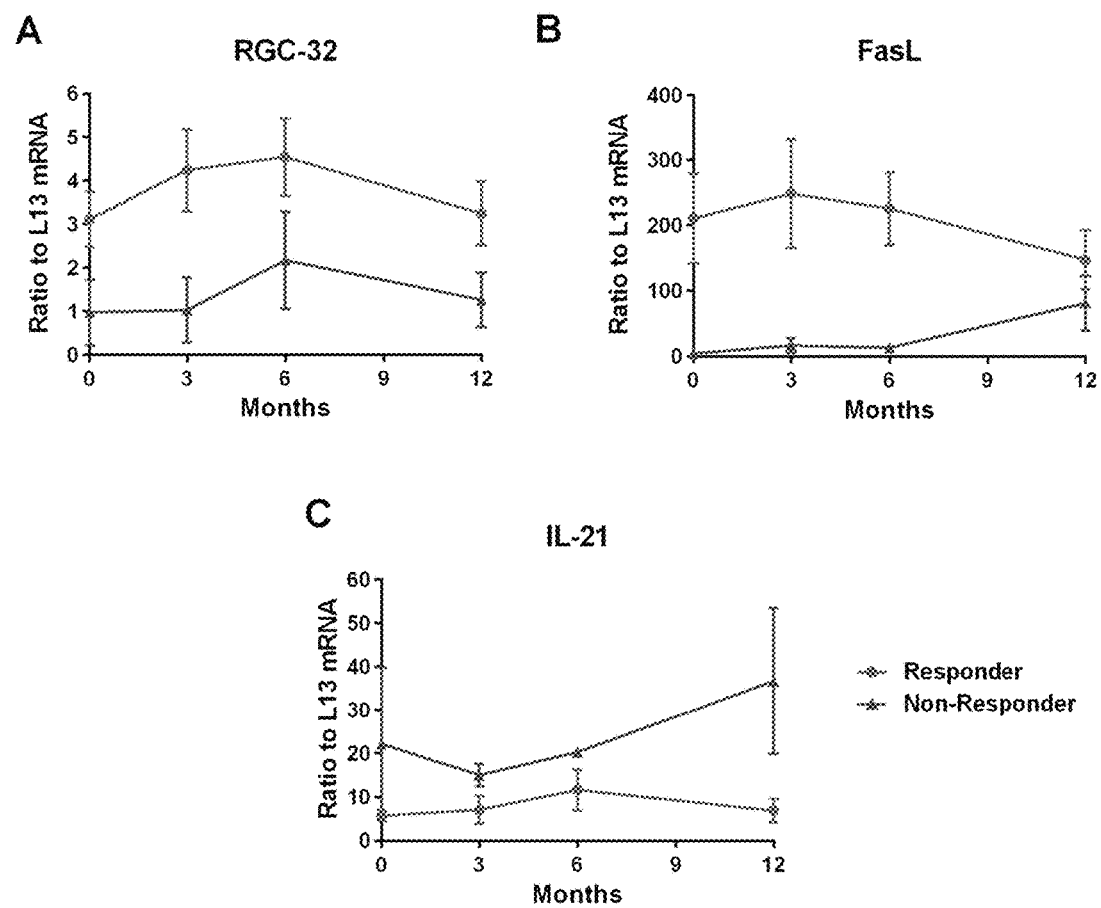
FIGS. 15A-15C. Time course of RGC-32, FasL, and IL-21mRNA expression in GA-treated MS patients. PBMCs were obtained from patients with RRMS at 0, 3, 6, and 12 months following the initiation of GA treatment. Target gene mRNA expression was measured in patient PBMCs using real-time qRT-PCR and expressed as a ratio to L13.

Over time, responders to GA showed persistently higher levels of RGC-32, whereas non-responders showed persistently lower levels (FIG. 15A). A similar pattern was observed for FasL (FIG. 15B), with higher levels of mRNA expression seen in responders and lower levels seen in non-responders over time. Conversely, over time responders to GA showed persistently lower levels of IL-21, whereas non-responders showed persistently higher levels (FIG. 15C). CDC2 and AKT mRNA expression did not exhibit a pattern that differed between responders and non-responders over time (data not shown).

Figures 16A, 16B:
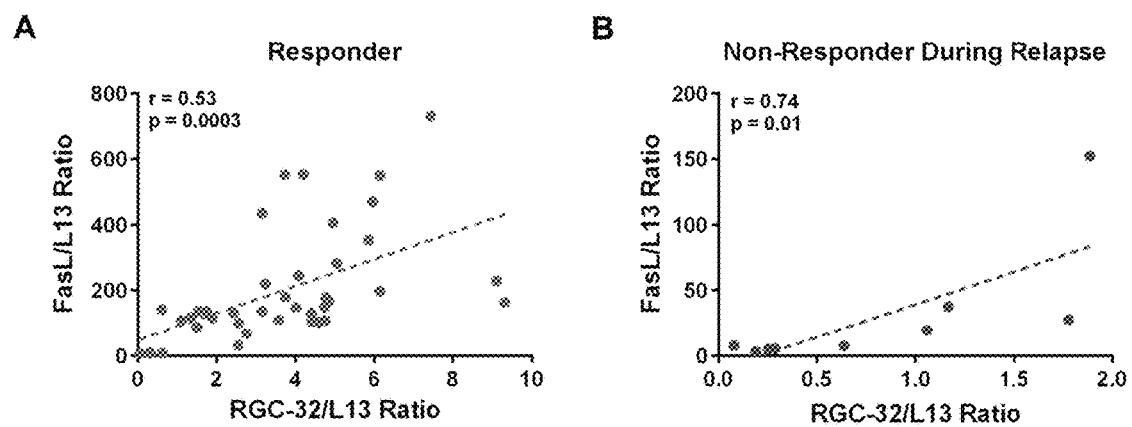
FIGS. 16A-16B. Correlation of RGC-32 and FasL mRNA in GA-treated MS patients. RGC-32 mRNA levels were correlated with those of FasL in both responders (FIG. 16A) and non-responders during relapses (FIG. 16B). The Pearson correlation coefficient for responders was r=0.53 (p=0.0003), and r=0.74 (p=0.01) for non-responders.

Furthermore, RGC-32 and FasL mRNA levels were positively correlated within responders during periods of both remission and relapse, as well as non-responders during relapse (FIG. 16A, B). Pearson correlation coefficients were r=0.53 (p=0.0003) for responders and r=0.74 (p=0.01) for non-responders during relapse. No statistically significant correlations were found between EDSS scores and any of the target genes examined (data not shown).

ROC Analysis

Figures 17A, 17B, 17C:
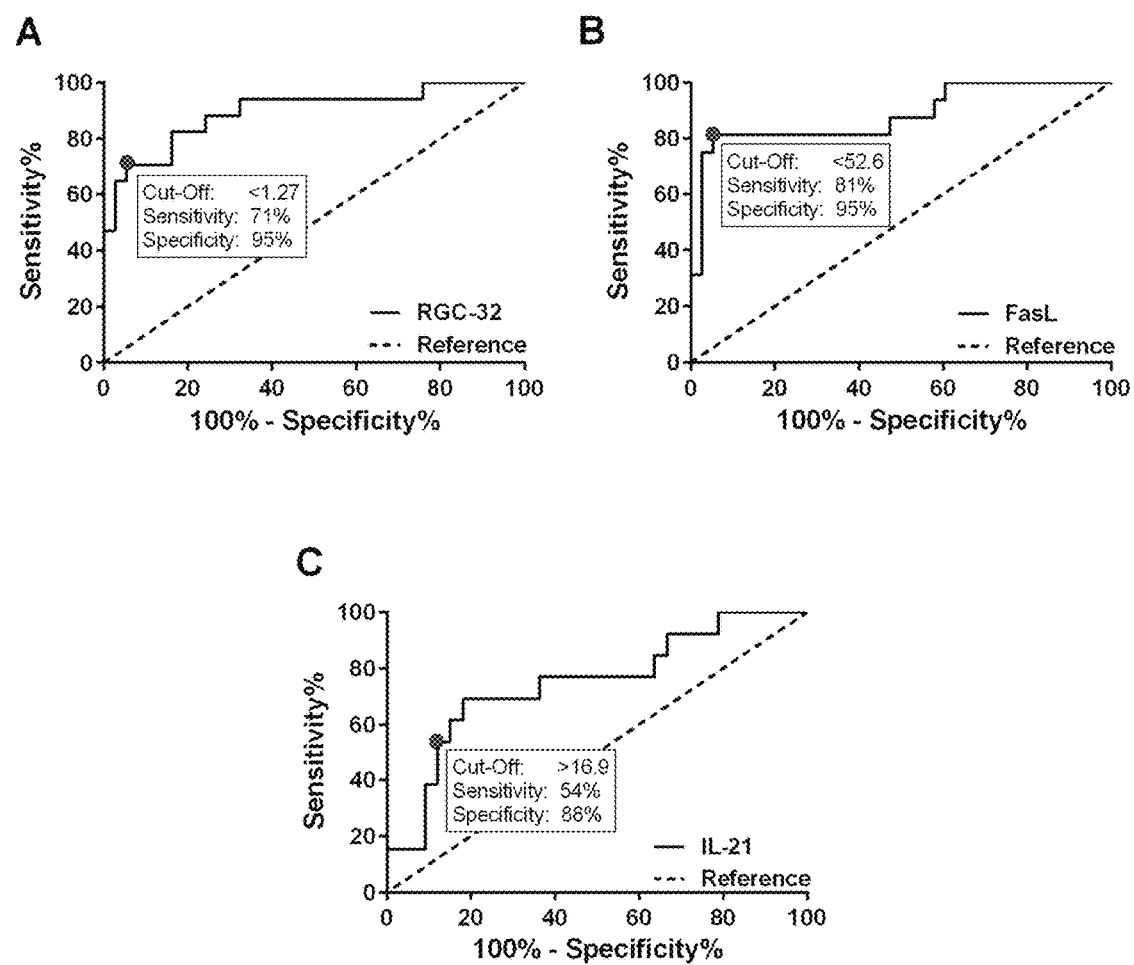
FIGS. 17A-17C. ROC curve analysis to assess the predictive accuracy of RGC-32, FasL, and IL-21 mRNA in detecting MS patient relapse. The probability (C-statistic, or AUC) of accurately detecting relapse was 90% using RGC-32 (p<0.0001), 88% using FasL (p<0.0001), and 75% using IL-21 (p=0.01).

ROC analysis was used to assess the predictive accuracy of using mRNA levels of each putative biomarker to detect patient relapse. The probability (C-statistic, or AUC) of accurately detecting relapse was 90% using RGC-32 (95% CI 80-99%, p<0.0001), 88% using FasL (95% CI 77-99%, p<0.0001), and 75% using IL-21 (95% CI 58-91%, p=0.01) (FIG. 17). In the present cohort, a RGC-32/L13 ratio<1.27 detected patient relapse with a sensitivity of 71% (95% CI 44-90%) and a specificity of 95% (95% CI 82-99%) (FIG. 17A). A FasL/L13 ratio<52.6 detected patient relapse with a sensitivity of 81% (95% CI 54-96%) and a specificity of 95% (95% CI 82-99%) (FIG. 17B). An IL-21/L13 ratio>16.9 detected patient relapse with a sensitivity of 54% (95% CI 25-81%) and a specificity of 88% (95% CI 72-97) (FIG. 17C).

Figures 18A, 18B, 18C:
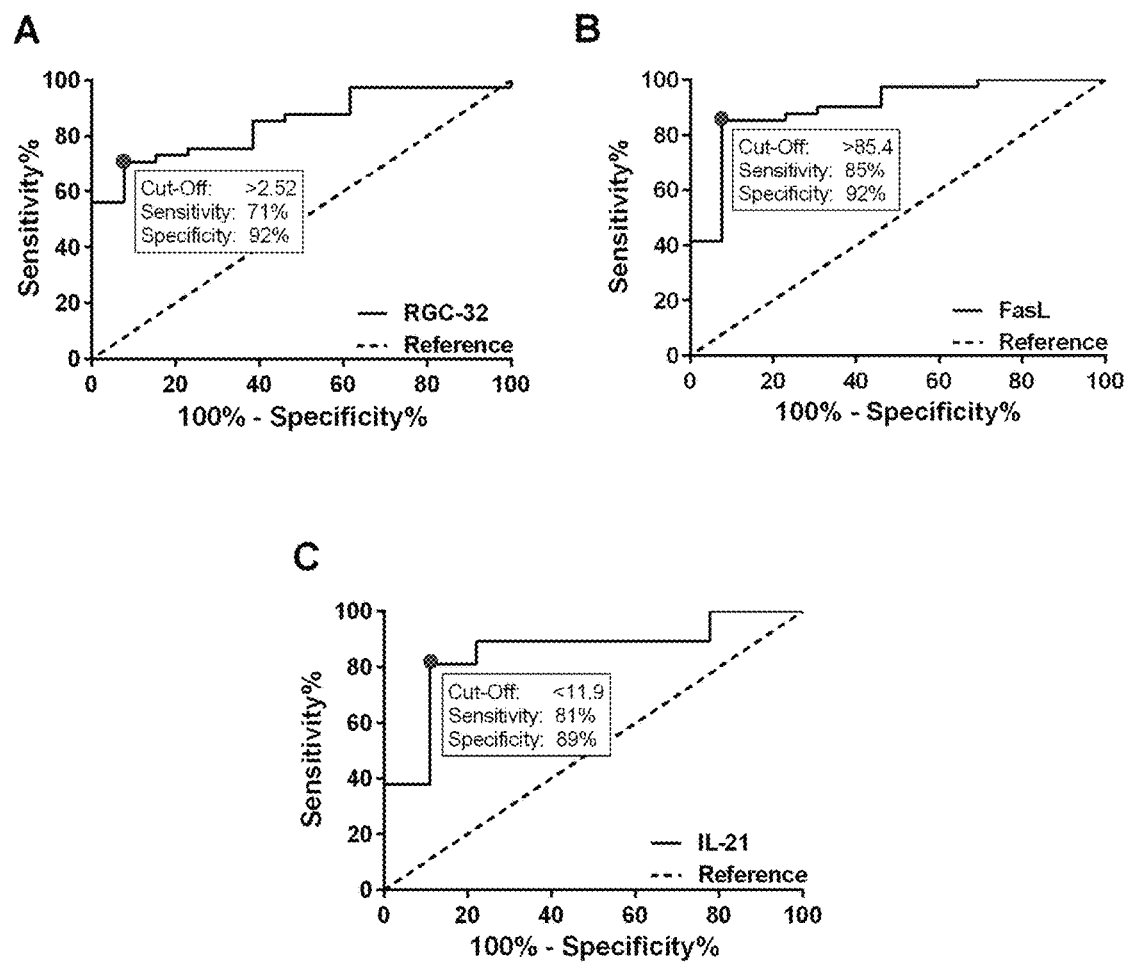
FIGS. 18A-18C. ROC curve analysis to assess the predictive accuracy of RGC-32, FasL, and IL-21 mRNA in detecting MS patient response to GA. The probability (C-statistic, or AUC) of accurately detecting response to GA treatment over 2 years was 85% using RGC-32 (p=0.0002), 90% using FasL (p<0.0001), and 85% using IL-21 (p=0.001).
Figure 19:
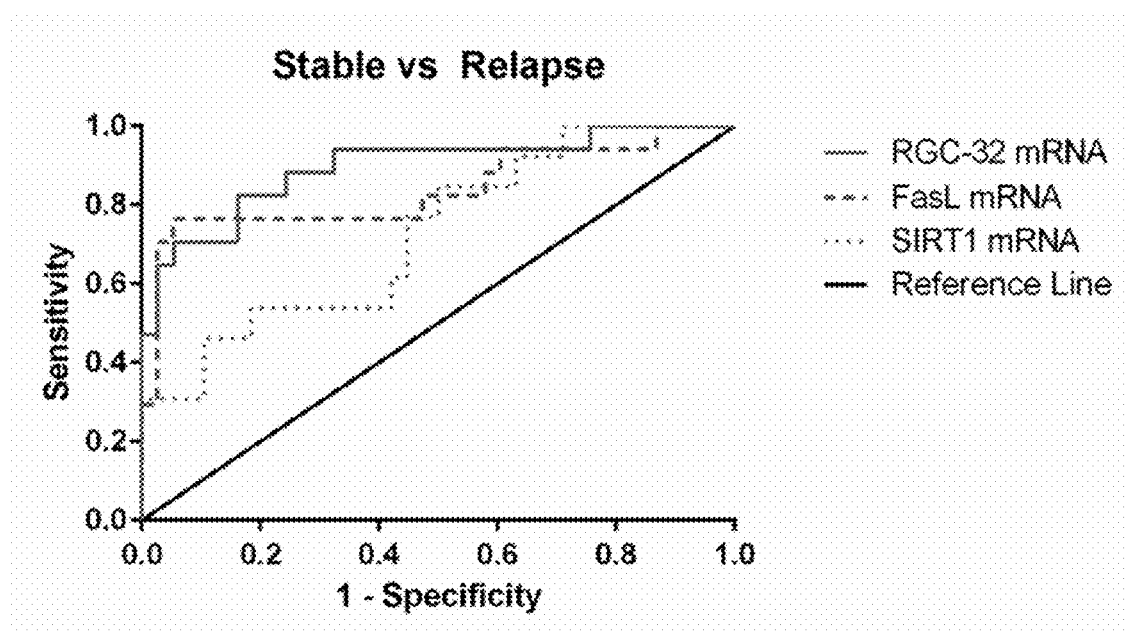
FIG. 19. ROC curve analysis to assess the predictive accuracy of RGC-32, FasL, and SIRT1 mRNA in detecting MS relapse. The probability (C-statistic, or AUC) of accurately detecting relapse was 90% using RGC-32 (p<0.0001), 88% using FasL (p<0.0001), and 72% using SIRT1 (p=0.02).

Since persistently higher levels of RGC-32 and FasL as well as lower levels of IL-21 mRNA were associated with a good response to GA treatment over time, ROC analysis was also used to assess the predictive accuracy of RGC-32, FasL, and IL-21 in detecting response to GA. The probability (C-statistic, or AUC) of accurately detecting response to GA treatment over 2 years was 85% using RGC-32 (95% CI 74-95%, p=0.0002), 90% using FasL (95% CI 81-100%, p<0.0001), and 85% using IL-21 (95% CI 71-99%, p=0.001) (FIG. 18). In the present cohort, a RGC-32/L13 ratio>2.52 correctly detected patient response to GA with a sensitivity of 71% (95% CI 54-84%) and a specificity of 92% (95% CI 64-100%). A FasL/L13 ratio>85.4 correctly detected patient response to GA with a sensitivity of 85% (95% CI 71-94%) and a specificity of 92% (95% CI 64-100%). An IL-21/L13 ratio<11.9 correctly detected patient response to GA with a sensitivity of 81% (95% CI 65-92%) and a specificity of 89% (95% CI 52-100%).

Additionally, ROC curve analysis was performed using only baseline mRNA levels from samples collected prior to GA administration (i.e. at month 0) to assess the predictive accuracy of initial RGC-32, FasL, and IL-21 levels in predicting future response to GA. The probability (C-statistic, or AUC) of accurately predicting response to GA was 82% using RGC-32 (95% CI 58-100%, p=0.10), 100% using FasL (95% CI 100-100%, p=0.03), and 75% using IL-21 (95% CI 35-100%, p=0.28) (data not shown).

Additional ROC analysis data using four of the biomarkers (RGC-32, FasL, IL-21, SIRT1) is presented in Tables 3 and 4, and in FIG. 18. This data indicates that these four biomarkers alone or in combination could serve as potential biomarkers to predict relapses and response to treatment.

TABLE 3

Receiver operating characteristic (ROC) curve analysis to assess the predictive accuracy of RGC-32, FasL, IL-21, and SIRT1 mRNA in detecting MS patient relapse.

| | RGC-32 | FasL | IL-21 | SIRT1 |
|---|---|---|---|---|
| Area Under Curve | 90% (p < 0.0001) | 88% (p < 0.0001) | 75% (p = 0.001) | 88% (p < 0.047) |
| Cut-Off (Ratio to L13) | <1.27 | <52.6 | >16.9 | <3.06 |
| Sensitivity | 71% | 81% | 54% | 54% |
| Specificity | 95% | 95% | 88% | 81% |

AUC, represented as a percentage, with a perfect score being 100% predictability.
Cut-off was calculated as ratio of target gene to L13 (housekeeping gene).

TABLE 4

Receiver operating characteristic (ROC) curve analysis to assess the predictive accuracy of RGC-32, FasL, IL-21, and SIRT1 mRNA in detecting MS patient response to GA.

| | RGC-32 | FasL | IL-21 | SIRT1 |
|---|---|---|---|---|
| Area Under Curve | 85% (p = 0.0002) | 90% (p < 0.0001) | 85% (p = 0.001) | 88% (p < 0.047) |
| Cut-Off (Ratio to L13) | >2.52 | >85.4 | <11.9 | <0.645 |
| Sensitivity | 71% | 85% | 81% | 54% |
| Specificity | 92% | 92% | 89% | 80% |

AUC, represented as a percentage, with a perfect score being 100% predictability.
Cut-off was calculated as ratio of target gene to L13 (housekeeping gene).

Discussion

The data provided herein reveals that inflammatory cells (T cells and macrophages), OLG, and astrocytes all express SIRT1 in the MS brain. The expression of SIRT1 was not confined to the MS plaques but was also present in NAWM and NAGM areas, indicating a widespread distribution of cells expressing SIRT1.

To gain more insight into the role played by SIRT1 in inflammatory cells, the expression of SIRT1 mRNA in PBMCs was examined, in relation to disease activity in MS patients. This analysis was performed in unstimulated PBMCs in order to mimic the in vivo situation as closely as possible (Lopatinskaya et al., 2003). The levels of SIRT1 were found to be significantly decreased in the PBMCs of MS patients with relapses when compared to those of healthy controls. These data suggest that low levels of SIRT1 can be used a possible biomarker of disease activity in MS patients.

To further investigate the factors that might regulate SIRT1 expression, it was asked whether RGC-32 might be involved in SIRT1 expression. It was found that silencing of RGC-32 in PBMCs led to a significant decrease in SIRT1 expression. These data suggest that the expression of SIRT1 is regulated by RGC-32, and they confirm previous observations in cancer cell lines (Vlaicu et al., 2013; Vlaicu et al., 2010). This finding is important because RGC-32 was found to promote cell cycle activation and survival through the activation of the cdc2/cyclinB1 complex (Badea et al., 2002; Badea et al., 1998), which also phosphorylates and activates SIRT1 (Sasaki et al., 2008). This data suggest that regulation of SIRT1 expression is an additional mechanism by which RGC-32 promotes survival. It is also entirely possible that the low levels of RGC-32 expression seen in the PBMCs of MS patients with relapses are responsible for the reduction in SIRT1 expression seen during the active phase of the disease.

To further investigate the relationship between SIRT1 and T-cell survival, the effect of the SIRT1 inhibitor sirtinol on apoptosis and FasL expression was examined. It was found that the expression of FasL was significantly increased, indicating that FasL expression is, at least in part, SIRT1-dependent. In addition, inhibition of SIRT1 leads to significant apoptosis in Jurkat cells and in $CD4^+$ and $CD8^+$ from patients with MS. These results showing a decreased level of SIRT1 in MS patients with relapses are in agreement with recent data obtained in EAE, an animal model of MS. These experiments showed that administration of resveratrol, a SIRT1 activator, ameliorates the disease course in EAE (Nimmagadda et al., 2013). In addition, resveratrol was found to trigger apoptosis in activated T cells and also to induce a decrease in spinal cord inflammation during EAE (Singh et al., 2007). Resveratrol was also found to be neuroprotective (Shindler et al., 2010), and the mechanism for its immunomodulatory and neuroprotective effects appears to involve the activation of SIRT1 (Singh et al., 2007).

ROC analysis showed that SIRT1 mRNA and protein levels accurately detected patient relapse and patient response to GA treatment.

In light of these initial studies, RGC-32, FasL, CDC2, AKT, and IL-21 were evaluated as potential biomarkers of relapse and response to GA treatment in a cohort of MS patients over time. This analysis was also performed in unstimulated PBMCs in order to mimic the in vivo situation as closely as possible, so that alterations in mRNA expression would have greater predictive value with respect to clinical exacerbations (Lopatinskaya et al., 2003).

It was previously shown that RGC-32 and FasL mRNA levels are significantly decreased and that IL-21 levels are increased in the PBMCs of MS patients during clinical relapse compared to remission (Tegla et al., 2013). The present data extend and confirm these prior results in a greater number of patients. Furthermore, ROC analysis of this cohort showed that RGC-32, FasL, and IL-21 mRNA levels accurately detected patient relapse (FIG. 17). Together, these findings support the use of RGC-32, FasL, and IL-21 as potential serum biomarkers of disease activity in multiple sclerosis.

Overall, RGC-32 and FasL mRNA levels were significantly increased and IL-21 levels were decreased in the PBMCs of MS patients defined as responders compared to non-responders to GA. Over time, RGC-32 and FasL levels were persistently higher and IL-21 levels were persistently lower in responders versus non-responders as well. Furthermore, ROC analysis of this cohort showed that RGC-32, FasL, and IL-21 mRNA levels accurately detected patient response to GA (FIG. 18). Together, these findings show for the first time that RGC-32, FasL, and IL-21 are potential serum biomarkers of response to GA in multiple sclerosis.

The synchronized changes observed in RGC-32 and FasL mRNA expression within PBMCs either during relapses or with respect to GA therapy response may be explained by the known role of RGC-32 in the regulation of FasL expression (Tegla et al., 2013). Since RGC-32 binds to and up-regulates CDC2/cyclin B1 kinase activity (Badea et al., 2002; Fosbrink et al., 2009), FasL expression in T-cells is regulated in part by the CDC2/cyclin B1 complex (Torgler et al., 2004), and RGC-32 silencing significantly decreases FasL mRNA expression (Tegla et al., 2013), it is possible that RGC-32 regulates FasL expression by modulating the activity of the CDC2/cyclin B1 complex. These data also suggest that RGC-32 is involved in regulating T-cell apoptosis by modulating the expression of FasL (Tegla et al., 2013). In MS, myelin and myelin-producing oligodendrocytes in the CNS are targeted for autoimmune attack via antigen-specific CD4+ T cells (Rus et al., 2006). T-cell apoptosis in MS is regulated in part by the Fas-FasL system (Aktas et al., 2006), and ex vivo studies have demonstrated an increased resistance of T-cells to Fas-mediated apoptosis during MS relapses (Okuda et al., 2006). Thus, in this case a decrease in RGC-32 and an associated decrease in FasL expression may result in a decrease in FasL-mediated T-cell apoptosis, promote the survival of myelin-targeted T-cells, and result in the onset of clinical relapse and a suboptimal response to GA treatment.

It is less clear if and how IL-21 expression is regulated by RGC-32, although IL-21 is involved with T-cell proliferation and cell cycle activation. Preliminary experiments using CD4+ T-cells from RGC-32 knockout mice (Tegla et al., 2015) showed increased expression of IL-21 mRNA in the absence of RGC-32 in CD4+ T-cells stimulated with anti-CD3/CD28. These data suggest an inhibitory effect of RGC-32 on IL-21 transcription, which could potentially explain the inverse relationship between RGC-32 and IL-21 mRNA levels as observed in this study. However, further work is needed to confirm these preliminary results.

Overall, the data suggest that SIRT1, RGC-32, FasL and IL-21 could serve as serum biomarkers for the detection of MS patient relapse and response to GA therapy. Such information could potentially help guide treatment decisions, delay disease progression, and improve outcomes for MS patients.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

Badea, T., et al., 2002. RGC-32 increases p34CDC2 kinase activity and entry of aortic smooth muscle cells into S-phase. J Biol Chem. 277, 502-8.

Badea, T. C., et al., 1998. Molecular cloning and characterization of RGC-32, a novel gene induced by complement activation in oligodendrocytes. J Biol Chem. 273, 26977-81.

Baur, J. A., 2010. Biochemical effects of SIRT1 activators. Biochim Biophys Acta 1804, 1626-1634.

Bouras, T., et al., 2005. SIRT1 deacetylation and repression of p300 involves lysine residues 1020/1024 within the cell cycle regulatory domain 1. J Biol Chem. 280, 10264-76.

Brunet, A., et al., 2004. Stress-dependent regulation of FOXO transcription factors by the SIRT1 deacetylase. Science. 303, 2011-5.

Camelo, S., et al., 2005. Transcriptional therapy with the histone deacetylase inhibitor trichostatin A ameliorates experimental autoimmune encephalomyelitis. J Neuroimmunol. 164, 10-21.

Chen, D., et al., 2008. Tissue-specific regulation of SIRT1 by calorie restriction. Genes Dev. 22, 1753-7.

Compston, A., Coles, A., 2008. Multiple sclerosis. Lancet. 372, 1502-17.

Costantino, C. M., et al., 2008. Multiple sclerosis and regulatory T cells. J Clin Immunol. 28, 697-706.

Cudrici, C., et al., 2007. Dendritic cells are abundant in non-lesional gray matter in multiple sclerosis. Exp Mol Pathol. 83, 198-206.

Fonseca-Kelly, Z., et al., 2012. Resveratrol Neuroprotection in a Chronic Mouse Model of Multiple Sclerosis. Front Neurol. 3, 84.

Fosbrink, M., et al., 2005. Overexpression of RGC-32 in colon cancer and other tumors. Exp Mol Pathol. 78, 116-22.

Frohman, E. M., et al., 2006. Multiple Sclerosis—The Plaque and Its Pathogenesis. New Engl J Med. 354, 942-955.

Grobner, T. 2006. Gadolinium—a specific trigger for the development of nephrogenic fibrosing dermopathy and nephrogenic systemic fibrosis? Nephrol. Dial. Transplant. 21:1104-1108.

Guarente, L., 2011. Franklin H. Epstein Lecture: Sirtuins, aging, and medicine. N Engl J Med. 364, 2235-44.

He, W., et al., 2012. Mitochondrial sirtuins: regulators of protein acylation and metabolism. Trends Endocrinol Metab. 23, 467-76.

Hellman, R. 2011. Gadolinium-Induced Nephrogenic Systemic Fibrosis. Seminars in Nephrology 31:310-316.

Imai, S., et al., 2000. Transcriptional silencing and longevity protein Sir2 is an NAD-dependent histone deacetylase. Nature. 403, 795-800.

Imler, T. J., Petro, T. M., 2009. Decreased severity of experimental autoimmune encephalomyelitis during resveratrol administration is associated with increased IL-17+IL-10+ T cells, CD4-IFN-γ+ cells, and decreased macrophage IL-6 expression. Int Immunopharmacol. 9, 134-143.

Keegan, B. M., Noseworthy, J. H., 2002. Multiple sclerosis. Annu Rev Med. 53, 285-302.

Koch, M. W., et al., 2013a. Epigenetic changes in patients with multiple sclerosis. Nat Rev Neurol. 9, 35-43.

Koch, M. W., et al., 2013b. Epigenetics and miRNAs in the diagnosis and treatment of multiple sclerosis. Trends Mol Med. 19, 23-30.

Kurtzke, J. F., 1983. Rating neurologic impairment in multiple sclerosis: an expanded disability status scale (EDSS). Neurology. 33, 1444-52.

Lopatinskaya, L., et al., 2003. The development of clinical activity in relapsing-remitting MS is associated with a decrease of FasL mRNA and an increase of Fas mRNA in peripheral blood. J Neuroimmunol. 138, 123-31.

Lublin, F. D., et al., 2014. Defining the clinical course of multiple sclerosis: the 2013 revisions. Neurology 83:278-86.

Luo, J., et al., 2000. Deacetylation of p53 modulates its effect on cell growth and apoptosis. Nature. 408, 377-81.

Martinez-Pasamar, S., et al., 2013. Dynamic cross-regulation of antigen-specific effector and regulatory T cell subpopulations and microglia in brain autoimmunity. BMC Syst Biol. 7, 34.

McDonald, W. I., et al., 2001. Recommended diagnostic criteria for multiple sclerosis: guidelines from the International Panel on the diagnosis of multiple sclerosis. Ann Neurol. 50, 121-7.

Motta, M. C., et al., 2004. Mammalian SIRT1 represses forkhead transcription factors. Cell. 116, 551-63.

Niculescu, F., et al., 1997. Activation of Ras and mitogen-activated protein kinase pathway by terminal complement complexes is G protein dependent. J Immunol. 158, 4405-12.

Nimmagadda, V. K., et al., 2013. Overexpression of SIRT1 Protein in Neurons Protects against Experimental Autoimmune Encephalomyelitis through Activation of Multiple SIRT1 Targets. J Immunol. 190, 4595-4607.

Penberthy, W. T., Tsunoda, I., 2009. The importance of NAD in multiple sclerosis. Curr Pharm Des. 15, 64-99.

Petro, T. M., 2011. Regulatory role of resveratrol on Th17 in autoimmune disease. Int Immunopharmacol. 11, 310-318.

Polman, C. H., et al., 2005. Diagnostic criteria for multiple sclerosis: 2005 revisions to the "McDonald Criteria". Ann Neurol. 58, 840-6.

Polman, C. H., et al., 2011. Diagnostic criteria for multiple sclerosis: 2010 revisions to the McDonald criteria. Ann. Neurol. 69:292-302.

Rus, H. G., et al., 1996a. Sublytic complement attack induces cell cycle in oligodendrocytes. J Immunol. 156, 4892-900.

Rus, H. G., et al., 1996b. Interleukin-6 and interleukin-8 protein and gene expression in human arterial atherosclerotic wall. Atherosclerosis. 127, 263-71.

Sasaki, T., et al., 2008. Phosphorylation regulates SIRT1 function. PLoS One. 3, e4020.

Sengupta, N., Seto, E., 2004. Regulation of histone deacetylase activities. J Cell Biochem. 93, 57-67.

Shindler, K. S., et al., 2010. Oral Resveratrol Reduces Neuronal Damage in a Model of Multiple Sclerosis. J Neuroophthalmol. 30, 328-339.

Singh, N. P., et al., 2007. Resveratrol (trans-3,5,4'-Trihydroxystilbene) Ameliorates Experimental Allergic Encephalomyelitis, Primarily via Induction of Apoptosis in T Cells Involving Activation of Aryl Hydrocarbon Receptor and Estrogen Receptor. Mol Pharmacol. 72, 1508-1521.

Smith, J. S., et al., 2000. A phylogenetically conserved NAD+-dependent protein deacetylase activity in the Sir2 protein family. Proc Natl Acad Sci USA. 97, 6658-63.

Tegla, C. A., et al., 2013. Dual role of Response gene to complement-32 in multiple sclerosis. Exp Mol Pathol. 94, 17-28.

Turner, B. M., 1998. Histone acetylation as an epigenetic determinant of long-term transcriptional competence. Cell Mol Life Sci. 54, 21-31.

Vaquero, A., et al., 2007. SIRT1 regulates the histone methyl-transferase SUV39H1 during heterochromatin formation. Nature. 450, 440-44.

Vaquero, A., et al., 2004. Human SirT1 interacts with histone H1 and promotes formation of facultative heterochromatin. Mol Cell. 16, 93-105.

Vlaicu, S. I., et al., 2013. Role of C5b-9 complement complex and response gene to complement-32 (RGC-32) in cancer. Immunol Res. 56, 109-21.

Vlaicu, S. I., et al., 2010. Epigenetic modifications induced by RGC-32 in colon cancer. Exp Mol Pathol. 88, 67-76.

Wang, C., et al., 2014. Visualizing epigenetics: Current advances and advantages in HDAC PET imaging techniques. Neuroscience. 264, 186-97.

Wang, P., et al., 2011. Nicotinamide phosphoribosyltransferase protects against ischemic stroke through SIRT1-dependent adenosine monophosphate-activated kinase pathway. Ann Neurol. 69, 360-74.

Yeung, F., et al., 2004. Modulation of NF-kappaB-dependent transcription and cell survival by the SIRT1 deacetylase. EMBO J. 23, 2369-80.

Zhang, F., et al., 2011. Role of HDAC3 on p53 expression and apoptosis in T cells of patients with multiple sclerosis. PLoS One. 6, e16795.

Zhang, J., et al., 2009. The type III histone deacetylase Sirt1 is essential for maintenance of T cell tolerance in mice. J Clin Invest. 119, 3048-58.

Zhang, T., Kraus, W. L., 2010. SIRT1-dependent regulation of chromatin and transcription:

Linking NAD+ metabolism and signaling to the control of cellular functions. Biochim Biophys Acta 1804, 1666-1675.

Zhang, X., et al., 2005. Histone deacetylase 3 (HDAC3) activity is regulated by interaction with protein serine/threonine phosphatase 4. Genes Dev. 19, 827-39.

What is claimed is:

1. A method of treating a subject having relapsing-remitting multiple sclerosis (RRMS) that is undergoing relapse of the disease, comprising:
   (a) determining mRNA expression levels for one or more of biomarkers SIRT1 and RGC-32 in a population of cells isolated from a subject having RRMS,
   (b) determining the mRNA expression level for L13 in the same population of cells,
   (c) selecting SIRT1 as the biomarker and calculating a SIRT1/L13 ratio of <3.06+/−10%, or selecting RGC-32 as the biomarker and calculating a RGC-32/L13 ratio of <1.27+/−10%,
   (d) diagnosing the subject in (c) as undergoing relapse, and
   (e) administering a therapeutically effective amount of a treatment for RRMS to the subject diagnosed in (d).

2. The method of claim 1 comprising selecting SIRT1 as the biomarker and calculating a SIRT1/L13 ratio of <3.06+/−10%.

3. The method of claim 1 comprising selecting RGC-32 as the biomarker and calculating a RGC-32/L13 ratio of <1.27+/−10%.

4. The method of claim 1, wherein mRNA expression levels for both biomarkers are determined.

5. The method of claim 1, wherein the treatment is selected from the group consisting of glatiramer acetate (GA), beta-interferons, teriflunomide, fingolimod, dimethyl fumarate, and natalizumab.

6. The method of claim 1, wherein the population of cells is selected from the group consisting of peripheral blood mononuclear cells (PBMCs), CD4+ T cells, CD8+ T cells, MAB328+ cells, GFAP+ cells, leukocytes, monocytes, glial cells, dendritic cells, and neurons.

7. The method of claim 1, wherein the treatment is glatiramer acetate (GA).

8. The method of claim 1, wherein the population of cells is peripheral blood mononuclear cells (PBMCs).

* * * * *